(12) United States Patent
Zhao et al.

(10) Patent No.: US 11,464,724 B2
(45) Date of Patent: Oct. 11, 2022

(54) LOW SHEAR STRESS CONDITIONER COMPOSITION WITH SPHERICAL GEL NETWORK VESICLES

(71) Applicant: The Procter & Gamble Company, Cincinnati, OH (US)

(72) Inventors: Jean Jianqun Zhao, Cincinnati, OH (US); Toshiyuki Iwata, Singapore (SG); Zhicai Zhou, Singapore (SG); Robert Wayne Glenn, Jr., Liberty Township, OH (US); Xiaoru Jenny Wang, Mason, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 16/677,921

(22) Filed: Nov. 8, 2019

(65) Prior Publication Data
US 2020/0146955 A1 May 14, 2020

Related U.S. Application Data

(60) Provisional application No. 62/757,411, filed on Nov. 8, 2018.

(51) Int. Cl.
*A61K 8/41* (2006.01)
*A61K 8/04* (2006.01)
(Continued)

(52) U.S. Cl.
CPC .............. *A61K 8/416* (2013.01); *A61K 8/046* (2013.01); *A61K 8/14* (2013.01); *A61K 8/342* (2013.01); *A61Q 5/12* (2013.01); *A61K 2800/87* (2013.01)

(58) Field of Classification Search
CPC . A61Q 5/02; A61Q 5/12; A61Q 19/00; A61Q 19/10; A61Q 17/04; A61Q 5/006;
(Continued)

(56) References Cited

U.S. PATENT DOCUMENTS 3,236,733 A    2/1966  Karsten
3,754,557 A    8/1973  Moore
(Continued)

FOREIGN PATENT DOCUMENTS

CN    101342117 B    9/2010
DE    10304721 B4    3/2007
(Continued)

OTHER PUBLICATIONS

Awad, T. et al., Colloidal structure and physical properties of gel networks containing anionic surfactant and fatty alcohol mixture, 2011, Journal of Dispersion Science and Technology, 32,807-815 (Year: 2011).*

(Continued)

*Primary Examiner* — Bethany P Barham
*Assistant Examiner* — Ayaan A Alam
(74) *Attorney, Agent, or Firm* — Kathleen Y Carter; Alexandra S Anoff

(57) ABSTRACT

A hair conditioner composition with a gel network that can contain a fatty alcohol and a cationic surfactant having a chloride counterion. The gel network composition can contain a uniform lamellar structure that comprises all vesicles or mostly vesicles.

16 Claims, 5 Drawing Sheets

(51) Int. Cl.
   *A61K 8/14* (2006.01)
   *A61K 8/34* (2006.01)
   *A61Q 5/12* (2006.01)

(58) Field of Classification Search
   CPC .......... A61Q 1/02; A61Q 19/002; A61Q 1/04;
   A61Q 1/10; A61Q 5/06; A61Q 19/08;
   A61Q 1/06; A61Q 3/00; A61Q 3/02;
   A61Q 7/02; A61Q 19/001; A61Q 1/12;
   A61Q 19/04; A61Q 19/02; A61Q 5/00;
   A61Q 5/004; A61Q 19/004; A61Q
   19/008; A61Q 7/00; A61Q 15/00; A61Q
   19/06; A61Q 1/14; A61Q 17/00; A61Q
   9/00; A61Q 19/007; A61Q 5/002; A61Q
   5/065; A61Q 5/10; A61K 8/416; A61K
   8/046; A61K 8/14; A61K 8/342; A61K
   2800/87
   See application file for complete search history.

(56) References Cited

U.S. PATENT DOCUMENTS

| | | | |
|---|---|---|---|
| 3,938,708 A | 2/1976 | Burger | |
| 4,607,756 A | 8/1986 | Courtman | |
| 4,610,874 A | 9/1986 | Matravers | |
| 4,880,618 A | 11/1989 | Grollier et al. | |
| 5,012,978 A | 5/1991 | Bolduc | |
| 5,077,040 A | 12/1991 | Bergmann et al. | |
| 5,213,792 A | 5/1993 | Grundmann et al. | |
| 5,635,469 A | 6/1997 | Fowler et al. | |
| 5,636,770 A | 6/1997 | Hachinohe et al. | |
| 5,674,478 A | 10/1997 | Dodd et al. | |
| 5,985,295 A | 11/1999 | Peffly | |
| 6,039,036 A | 3/2000 | Padilla | |
| 6,039,936 A | 3/2000 | Restle | |
| 6,524,563 B1 | 2/2003 | Wire et al. | |
| 6,589,509 B2 | 7/2003 | Keller et al. | |
| 6,602,494 B1 | 8/2003 | Jahedshoar et al. | |
| 6,604,693 B2 | 8/2003 | Santagiuliana | |
| 6,605,577 B1 | 8/2003 | Harrison et al. | |
| 6,642,194 B2 | 11/2003 | Harrison et al. | |
| 6,656,458 B1 | 12/2003 | Philippe et al. | |
| 6,927,196 B2 | 8/2005 | Snyder et al. | |
| 7,001,594 B1 | 2/2006 | Peffly et al. | |
| 7,217,777 B2 | 5/2007 | Lange et al. | |
| 7,316,815 B2 | 1/2008 | Philippe et al. | |
| RE40,534 E | 10/2008 | Harrison et al. | |
| 7,455,195 B2 | 11/2008 | Mekata | |
| 7,462,585 B2 | 12/2008 | Uehara | |
| 7,470,651 B2 | 12/2008 | Uehara et al. | |
| 7,504,093 B2 | 3/2009 | Bracken et al. | |
| 7,759,378 B2 | 7/2010 | Philippe et al. | |
| 8,017,106 B2 | 9/2011 | Keller et al. | |
| 8,263,053 B2 | 9/2012 | Duvel et al. | |
| 8,475,777 B2 | 7/2013 | Rautschek | |
| 8,476,472 B2 | 7/2013 | Hojo et al. | |
| 8,642,021 B2 | 2/2014 | Brautigam et al. | |
| 8,697,040 B2 | 4/2014 | Duvel et al. | |
| 8,956,597 B2 | 2/2015 | Gesztesi et al. | |
| 8,999,306 B2 | 4/2015 | Duvel et al. | |
| 9,040,041 B2 | 5/2015 | Desjarlais | |
| 9,101,554 B2 | 8/2015 | Sakuma | |
| 9,255,184 B2 | 2/2016 | Paul | |
| 9,308,398 B2 | 4/2016 | Hutton et al. | |
| 9,358,186 B2 | 6/2016 | Chandra et al. | |
| 9,539,199 B2 | 1/2017 | Beer et al. | |
| 9,539,208 B2 | 1/2017 | Tamarkin et al. | |
| 9,540,489 B2 | 1/2017 | Panandiker et al. | |
| 9,717,676 B2 | 8/2017 | Gartstein | |
| 9,828,170 B2 | 11/2017 | Nomura et al. | |
| 9,993,419 B2 | 6/2018 | Glenn, Jr. et al. | |
| 9,993,420 B2 | 6/2018 | Glenn, Jr. et al. | |
| 10,123,963 B2 | 11/2018 | Glenn, Jr. et al. | |
| 10,124,951 B2 | 11/2018 | Glenn, Jr. et al. | |
| 10,258,548 B2 | 4/2019 | Zhao | |
| 10,265,251 B2 | 4/2019 | Glenn, Jr. | |
| 10,265,255 B2 | 4/2019 | Glenn, Jr. | |
| 10,265,256 B2 | 4/2019 | Glenn, Jr. | |
| 10,285,925 B2 | 5/2019 | Glenn, Jr. | |
| 10,294,013 B2 | 5/2019 | Callens | |
| 10,322,012 B2 | 6/2019 | Palmatier et al. | |
| 10,322,072 B2 | 6/2019 | Glenn, Jr. | |
| 10,806,688 B2 | 10/2020 | Stella | |
| 10,828,248 B2 | 11/2020 | Glenn, Jr. | |
| 10,835,480 B2 | 11/2020 | Glenn, Jr. | |
| 2001/0006621 A1 | 7/2001 | Coupe | |
| 2001/0008630 A1 | 7/2001 | Pyles et al. | |
| 2001/0025857 A1 | 10/2001 | Baudin | |
| 2002/0031532 A1 | 3/2002 | Uchiyama | |
| 2002/0096184 A1 | 7/2002 | Elmer | |
| 2002/0143063 A1 | 10/2002 | Alvarado | |
| 2002/0197213 A1 | 12/2002 | Schmenger et al. | |
| 2002/0197219 A1 | 12/2002 | Seiberg | |
| 2003/0053961 A1 | 3/2003 | Eccard | |
| 2003/0152542 A1 | 8/2003 | Decoster et al. | |
| 2003/0228272 A1 | 12/2003 | Amjad et al. | |
| 2004/0018164 A1 | 1/2004 | Zofchak et al. | |
| 2004/0076595 A1 | 4/2004 | Khan | |
| 2004/0229763 A1 | 11/2004 | Hutton, III et al. | |
| 2004/0247550 A1 | 12/2004 | Asari et al. | |
| 2005/0002892 A1 | 1/2005 | Khan et al. | |
| 2005/0136011 A1 | 6/2005 | Nekludoff et al. | |
| 2005/0143268 A1* | 6/2005 | Midha | A61K 8/442 510/130 |
| 2005/0196372 A1 | 9/2005 | Cajan et al. | |
| 2005/0196376 A1 | 9/2005 | Loomis | |
| 2005/0197421 A1 | 9/2005 | Loomis | |
| 2005/0222001 A1 | 10/2005 | Baumeister et al. | |
| 2005/0274737 A1 | 12/2005 | Krause et al. | |
| 2006/0034792 A1 | 2/2006 | Lazzeri et al. | |
| 2006/0054634 A1 | 3/2006 | Mekata | |
| 2006/0078583 A1 | 4/2006 | Rennie et al. | |
| 2006/0083704 A1 | 4/2006 | Torgerson | |
| 2006/0275245 A1 | 12/2006 | Decoster et al. | |
| 2006/0292104 A1 | 12/2006 | Guskey et al. | |
| 2006/0293197 A1 | 12/2006 | Uehara et al. | |
| 2007/0179207 A1 | 8/2007 | Fernandez de Castro et al. | |
| 2007/0286837 A1 | 12/2007 | Torgerson et al. | |
| 2008/0066773 A1 | 3/2008 | Anderson et al. | |
| 2008/0138296 A1 | 6/2008 | Tamarkin et al. | |
| 2008/0292560 A1 | 11/2008 | Tamarkin et al. | |
| 2008/0292574 A1 | 11/2008 | Uehara | |
| 2009/0041706 A1 | 2/2009 | Molenda et al. | |
| 2009/0155383 A1 | 6/2009 | Kitko et al. | |
| 2009/0220448 A1 | 9/2009 | Iwata et al. | |
| 2009/0232759 A1 | 9/2009 | Bell et al. | |
| 2010/0092405 A1 | 4/2010 | Philippe et al. | |
| 2010/0143280 A1 | 6/2010 | Yokogi et al. | |
| 2010/0143281 A1 | 6/2010 | Okada et al. | |
| 2010/0143282 A1 | 6/2010 | Yokogi et al. | |
| 2010/0143425 A1 | 6/2010 | Okada et al. | |
| 2010/0178265 A1 | 7/2010 | Molenda et al. | |
| 2011/0135588 A1 | 6/2011 | Uehara et al. | |
| 2011/0171155 A1* | 7/2011 | Federle | C12N 9/90 424/70.24 |
| 2011/0226273 A1 | 9/2011 | Deardorff et al. | |
| 2011/0280110 A1 | 11/2011 | Chen | |
| 2011/0318295 A1 | 12/2011 | Shimizu et al. | |
| 2012/0020908 A1 | 1/2012 | Paul | |
| 2012/0031419 A1 | 2/2012 | Batt | |
| 2012/0034173 A1 | 2/2012 | Batt et al. | |
| 2012/0043352 A1 | 2/2012 | Rasmussen et al. | |
| 2012/0114819 A1 | 5/2012 | Ragnarsson et al. | |
| 2012/0171147 A1 | 7/2012 | Rautschek | |
| 2012/0288465 A1 | 11/2012 | Loechel | |
| 2013/0068849 A1 | 3/2013 | Birkel | |
| 2013/0075430 A1 | 3/2013 | Ragnarsson et al. | |
| 2013/0164244 A1 | 6/2013 | Molenda | |
| 2013/0202666 A1 | 8/2013 | Petkov et al. | |
| 2013/0280192 A1 | 10/2013 | Carter et al. | |
| 2013/0284196 A1 | 10/2013 | Murdock et al. | |
| 2013/0290192 A1 | 10/2013 | Johnson et al. | |
| 2014/0105943 A1 | 4/2014 | Pistorio et al. | |

(56) References Cited

U.S. PATENT DOCUMENTS

| | | |
|---|---|---|
| 2014/0107224 A1 | 4/2014 | Osman et al. |
| 2014/0116458 A1 | 5/2014 | Krueger |
| 2014/0135414 A1 | 5/2014 | Loomis |
| 2014/0166922 A1 | 6/2014 | Elsheikh |
| 2014/0216495 A1 | 8/2014 | Bureiko |
| 2014/0237732 A1 | 8/2014 | Zuedel Fernandes et al. |
| 2014/0261517 A1 | 9/2014 | Humphreys et al. |
| 2014/0302103 A1 | 10/2014 | Carter et al. |
| 2014/0348886 A1 | 11/2014 | Johnson et al. |
| 2014/0356303 A1 | 12/2014 | Rocco et al. |
| 2014/0377206 A1 | 12/2014 | Uehara et al. |
| 2015/0011450 A1 | 1/2015 | Carter et al. |
| 2015/0030643 A1 | 1/2015 | Gartstein et al. |
| 2015/0093420 A1 | 4/2015 | Snyder et al. |
| 2015/0190326 A1 | 7/2015 | Brouard et al. |
| 2015/0359725 A1 | 12/2015 | Glenn, Jr. et al. |
| 2015/0359726 A1 | 12/2015 | Glenn, Jr. et al. |
| 2015/0359727 A1 | 12/2015 | Glenn, Jr. et al. |
| 2015/0359728 A1 | 12/2015 | Glenn, Jr. et al. |
| 2016/0000673 A1 | 1/2016 | Ainger et al. |
| 2016/0143821 A1 | 5/2016 | Chang et al. |
| 2016/0309871 A1 | 10/2016 | Torres Rivera et al. |
| 2016/0310371 A1 | 10/2016 | Zhao et al. |
| 2016/0310372 A1 | 10/2016 | Glenn, Jr. et al. |
| 2016/0310375 A1 | 10/2016 | Torres Rivera et al. |
| 2016/0310376 A1 | 10/2016 | Torres Rivera et al. |
| 2016/0310377 A1 | 10/2016 | Torres Rivera et al. |
| 2016/0310397 A1 | 10/2016 | Johnson et al. |
| 2017/0087068 A1 | 3/2017 | Callens et al. |
| 2017/0165155 A1 | 6/2017 | Glenn, Jr. et al. |
| 2017/0165156 A1 | 6/2017 | Glenn, Jr. et al. |
| 2017/0165157 A1 | 6/2017 | Glenn, Jr. et al. |
| 2017/0165162 A1 | 6/2017 | Glenn, Jr. et al. |
| 2017/0165163 A1 | 6/2017 | Glenn, Jr. et al. |
| 2017/0165164 A1 | 6/2017 | Zhao et al. |
| 2017/0165165 A1 | 6/2017 | Zhao et al. |
| 2017/0165191 A1 | 6/2017 | Glenn, Jr. et al. |
| 2017/0174413 A1 | 6/2017 | Callens et al. |
| 2017/0246101 A1 | 8/2017 | Iwata |
| 2017/0304184 A1 | 10/2017 | Glenn, Jr. et al. |
| 2017/0304185 A1 | 10/2017 | Glenn, Jr. et al. |
| 2017/0304186 A1 | 10/2017 | Glenn, Jr. et al. |
| 2018/0098923 A1 | 4/2018 | Hutton, III |
| 2018/0168948 A1 | 6/2018 | Glenn, Jr. et al. |
| 2018/0168949 A1 | 6/2018 | Glenn, Jr. et al. |
| 2018/0168996 A1 | 6/2018 | Glenn, Jr. et al. |
| 2018/0221270 A1 | 8/2018 | Glenn, Jr. et al. |
| 2018/0256457 A1 | 9/2018 | Glenn, Jr. et al. |
| 2018/0256459 A1 | 9/2018 | Torres Rivera et al. |
| 2018/0256481 A1 | 9/2018 | Glenn, Jr. et al. |
| 2018/0353398 A1 | 12/2018 | Torres Rivera et al. |
| 2019/0328630 A1 | 10/2019 | Glenn, Jr. |
| 2019/0365633 A1 | 12/2019 | Glenn, Jr. |
| 2020/0146955 A1 | 5/2020 | Zhao |
| 2020/0170924 A1 | 6/2020 | Glenn, Jr. |

FOREIGN PATENT DOCUMENTS

| | | |
|---|---|---|
| EP | 978271 A1 | 2/2000 |
| EP | 1002525 A2 | 5/2000 |
| EP | 1340485 A2 | 2/2003 |
| EP | 2138155 A2 | 12/2009 |
| EP | 2883533 A1 | 6/2015 |
| JP | H06227941 A | 8/1994 |
| JP | H09175953 A | 7/1997 |
| JP | 2001247431 A | 9/2001 |
| JP | 2001302466 A | 10/2001 |
| JP | 3242689 B2 | 12/2001 |
| JP | 2003119113 A | 4/2003 |
| JP | 2005232271 A | 9/2005 |
| JP | 2006182743 A | 7/2006 |
| JP | 2010132569 A | 6/2010 |
| JP | 4694171 B2 | 6/2011 |
| JP | 2014125477 A | 7/2014 |
| JP | 2014234227 A | 12/2014 |
| WO | WO9619188 A1 | 6/1996 |
| WO | WO9720626 A1 | 6/1997 |
| WO | WO0222085 A1 | 3/2002 |
| WO | WO2004078901 A1 | 9/2004 |
| WO | WO2006045170 A2 | 5/2006 |
| WO | 2009016555 A1 | 2/2009 |
| WO | 2012004126 A2 | 1/2012 |
| WO | 2012084970 A1 | 6/2012 |
| WO | WO2013176666 A1 | 11/2013 |
| WO | WO2014204008 A1 | 12/2014 |

OTHER PUBLICATIONS

All final and non-final office actions for U.S. Appl. No. 15/843,069.
All final and non-final office actions for U.S. Appl. No. 15/843,146.
All final and non-final office actions for U.S. Appl. No. 15/843,178.
All final and non-final office actions for U.S. Appl. No. 15/946,275.
All final and non-final office actions for U.S. Appl. No. 15/972,763.
All final and non-final office actions for U.S. Appl. No. 15/973,845.
All final and non-final office actions for U.S. Appl. No. 15/978,667.
All final and non-final office actions for U.S. Appl. No. 16/104,343.
All final and non-final office actions for U.S. Appl. No. 16/439,801.
All final and non-final office actions for U.S. Appl. No. 16/537,794.
All final and non-final Office Actions, U.S. Appl. No. 14/739,588.
All final and non-final Office Actions, U.S. Appl. No. 14/739,670.
All final and non-final Office Actions, U.S. Appl. No. 14/739,708.
All final and non-final Office Actions, U.S. Appl. No. 14/739,755.
All final and non-final Office Actions, U.S. Appl. No. 15/135,684.
All final and non-final Office Actions, U.S. Appl. No. 15/135,705.
All final and non-final Office Actions, U.S. Appl. No. 15/135,712.
All final and non-final Office Actions, U.S. Appl. No. 15/135,715.
All final and non-final Office Actions, U.S. Appl. No. 15/136,020.
All final and non-final Office Actions, U.S. Appl. No. 15/136,032.
All final and non-final Office Actions, U.S. Appl. No. 15/274,226.
All final and non-final Office Actions, U.S. Appl. No. 15/380,194.
All final and non-final Office Actions, U.S. Appl. No. 15/380,218.
All final and non-final Office Actions, U.S. Appl. No. 15/380,261.
All final and non-final Office Actions, U.S. Appl. No. 15/380,293.
All final and non-final Office Actions, U.S. Appl. No. 15/380,345.
All final and non-final Office Actions, U.S. Appl. No. 15/380,373.
All final and non-final Office Actions, U.S. Appl. No. 15/381,298.
All final and non-final Office Actions, U.S. Appl. No. 15/492,429.
All final and non-final Office Actions, U.S. Appl. No. 15/492,451.
All final and non-final Office Actions, U.S. Appl. No. 15/492,469.
Anonymous "Shampoo only Scalp? Or entire head?—The Long Hair Community Discussion Boards", Feb. 1, 2011, Retrieved from the internet: URL: http://forums.longhaircommunity.com/archieve/index.php/t-91788.html, retrieved on Jul. 21, 2016.
Anonymous: "GNPD—Anti-Dandruff Shampoo", Nov. 1, 2012.
Anonymous: "GNPD—Anti-Dandruff Shampoo + Conditioner Set", Procter and Gamble China, Apr. 1, 2009, Mintel GNPD, Retrieved from the Internet: URL: http://www.gnpd.com/sinatra/recordpage/107827/from_search/EkXVQlu6vF/?page=2, Retrieved on Jul. 12, 2016.
Carolyn Evans: "Scalp Cleansing, Scalp Tonique, Hair Shampoo, Hair Conditioner, Demonstration" Youtube, Apr. 22, 2012, p. 2. First part of the video (0-3 min) dedicated to "scalp cleansing"; second part of the video (3-6 min) dedicated to the treatment of the hair.
Database GNPD Mintel; May 2014, "Coconut & Macadamia Oil Nourishing Shampoo and Nourishing Conditioner".
Database GNPD, Mintel; Aug. 2014 "Gold Olive Haircare Set".
Fabida. https://makeupandbeauty.com/head-shoulders-anti-dandruff-itchy-scalp-care-shampoo-review/. Published Jun. 26, 2012.
Free Sample, https://web.archive.org/web/20111116042029/http://freesampleprincess.com/head-and-shoulders-itchy-scalp-care-free-sample. Published Nov. 16, 2011.
Hair Conditioner Tips and Tricks. https://web.archive.org/web/20121106125731/http://www.thehairstyler.com/features/articles/hair-care/hair-conditioner-tips-and-tricks. Published Nov. 6, 2012.
In-Cosmetics 2012: Wacker Introduced Novel Silicone Emulsions and New Hybrid Polymer for Hair-Care and Hair-Styling Products, Apr. 2012.

(56) References Cited

OTHER PUBLICATIONS

Mommy Story, http://www.amommystory.com/2011/11/head-shoulders-eucalyptus-itchy-scalp-care-to-the-rescue-review-giveaway.html. Published Nov. 21, 2011.
PCT International Search Report and Written Opinion for PCT/US2015/035756 dated Dec. 21, 2015.
PCT International Search Report and Written Opinion for PCT/US2015/035796 dated Sep. 14, 2015.
PCT International Search Report and Written Opinion for PCT/US2015/035797 dated Sep. 14, 2015.
PCT International Search Report and Written Opinion for PCT/US2015/035799 dated Sep. 14, 2015.
PCT International Search Report and Written Opinion for PCT/US2016/028731 dated Jul. 5, 2016.
PCT International Search Report and Written Opinion for PCT/US2016/028739 dated Jul. 4, 2016.
PCT International Search Report and Written Opinion for PCT/US2016/028743 dated Jul. 25, 2016.
PCT International Search Report and Written Opinion for PCT/US2016/028745 dated Aug. 8, 2016.
PCT International Search Report and Written Opinion for PCT/US2016/028853 dated Sep. 30, 2016.
PCT International Search Report and Written Opinion for PCT/US2016/028855, dated Oct. 5, 2016.
PCT International Search Report and Written Opinion for PCT/US2016/028860 dated Jul. 7, 2016.
PCT International Search Report and Written Opinion for PCT/US2016/066753 dated Feb. 28, 2017.
PCT International Search Report and Written Opinion for PCT/US2016/066754 dated Feb. 20, 2017.
PCT International Search Report and Written Opinion for PCT/US2016/066755 dated Feb. 27, 2017.
PCT International Search Report and Written Opinion for PCT/US2016/066759 dated Feb. 27, 2017.
PCT International Search Report and Written Opinion for PCT/US2016/067916 dated Mar. 29, 2017.
PCT International Search Report and Written Opinion for PCT/US2017/028472 dated Jun. 29, 2017.
PCT International Search Report and Written Opinion for PCT/US2017/028473 dated Jun. 29, 2017.
PCT International Search Report and Written Opinion for PCT/US2017/028474 dated Jun. 29, 2017.
PCT International Search Report and Written Opinion for PCT/US2017/066561 dated Apr. 4, 2018.
PCT International Search Report and Written Opinion for PCT/US2017/066563 dated Apr. 4, 2018.
Samantha Zabell: "Mistakes You're Making Washing Your Hair—How You're Washing Your Hair Wrong", Jan. 14, 2014, Retrieved from the Internet: URL: http://www.goodhousekeeping.com/beauty/hair/tips/a19894/mistakes-washing-your-hair/, Section 3. "Overdoing it on shampoo and/or conditioner"; p. 2, retrieved on Jul. 21, 2016.
Silsoft* 253, amine functional silicone microemulsion, specialty fluids—personal care; Momentive marketing bulletin, publication date unknown.
Stylecaster, http://stylecaster.com/beauty/how-to-get-rid-of-dandruff/. Published: Jan. 16, 2014.
Xiameter Mem-0949 Emulsion (Nov. 2011).
"Clarifying Shampoo", Mintel, Jun. 2015.
"Reinforcing conditioner", Mintel, May 2014.
U.S. Appl. No. 16/537,794, filed Aug. 12, 2019, Glenn, Jr. et al.
"Colloidal and surface phenomena project—Hair Conditioner", http://www.courses.sens.buffalo.edu/ce457_527/ce457_pro/g8_doc.htm. Juan Carlos Alva Nieto et al., Published Apr. 9, 2002.
"How to Wash Your Hair to Minimize Hair Loss", by Haian, date and source unknown.
"I can control my hairstyle, a perfect hairstyle done within 5 minutes", Editor-in-Chief Jian Yu, Human Science and Technology Press, Aug. 2013.
All final and non-final office actions for U.S. Appl. No. 16/782,463.
Mommy Gearest, I must tell ya about Mustela: Foam Shampoo for Newborns, https://www.mommygearest.com/mustela-foam-shampoo-for-newborns-review. Published Apr. 11, 2012.
Olszanska, Chernik 201, 65, 10, p. 936-945, "Hair Conditioning Foam Formulations".
PCT International Search Report and Written Opinion for PCT/US2019/060371 dated Mar. 27, 2020.

* cited by examiner

LOW SHEAR STRESS CONDITIONER COMPOSITION WITH SPHERICAL GEL NETWORK VESICLES

FIELD OF THE INVENTION

The present invention relates to a conditioner composition, particularly a conditioner composition that has spherical gel network vesicles comprising a cationic surfactant having a chloride counterion.

BACKGROUND OF THE INVENTION

Consumers' hair and scalp require regular cleansing to remove sebum, which is secreted by the scalp, and other soils, which are deposited from the surrounding environment. The soiling of hair causes it to have a dirty feel and an unattractive appearance. Shampooing cleans the hair by removing excess soil and sebum. However, shampooing can leave the hair in a wet, tangled, and generally unmanageable state. Once the hair dries, it is often left in a dry, rough, lusterless, or frizzy condition due to removal of the hair's natural oils. Thus, many consumers treat their hair with conditioner products immediately after shampooing to mitigate this problem. Various delivery forms exist for hair conditioner products such as viscous liquids, creams, gels, mousses/foams, dissolvable solids, and sprays.

Today's liquid hair conditioners almost universally comprise a combination of (a) high levels of high melting point fatty compounds, the most common of which are C16 to C18 fatty alcohols and (b) cationic surfactants having at least one fatty carbon alkyl chain. These materials are typically mixed together in an aqueous carrier and at temperatures higher than their melting point to form lamellar structures, typically multilayer lamellar sheets. These lamellar sheets interact with each other to form a gel network (or a gel matrix as alternatively called) throughout the conditioner composition. The conditioner gel network contributes (a) to the phase stability of the composition in the case of the presence of insoluble hydrophobic conditioning agents by increasing its viscosity and yield value and (b) to the favorable in-use experience of the consumer, wet hair feel and wet hair combability.

Some consumers desire conditioner compositions in a foam form, including foams delivered by aerosol and mechanical foamers. Given the low density of the foam, conditioner ingredients such as surfactants and conditioning agents may be present at a higher concentration to deliver conditioning benefits in a reasonable volume of foam. The lamellar structure in combination with the concentrated composition can cause the composition to have a viscosity that is too high to produce a high-quality foam. In these cases, the produced foam is unattractive, less creamy, easily collapsed and has high viscosity.

As such, there remains a need for a hair conditioner composition with good stability and good wet feel that can be delivered as an attractive and creamy foam via an aerosol or mechanical foamer.

SUMMARY OF THE INVENTION

A hair conditioner composition comprising (a) a gel network composition comprising (i) from about 1 wt. % to about 10 wt. % of a cationic surfactant having a chloride counterion; and (ii) from about 1 wt. % to about 10 wt. % of a fatty alcohol selected from the group consisting of cetyl alcohol, stearyl alcohol, behenyl alcohol, and combinations thereof; wherein the gel network composition comprises all vesicles or mostly vesicles; (b) from about 60 wt. % to about 90 wt. % water; (c) from about 1 wt. % to about 10 wt. % propellant; wherein the mole ratio of cationic surfactant to fatty alcohol is from about 0.55 to about 1.2; wherein the composition comprises a liquid phase viscosity from about 5 cps to about 10,000 cP.

BRIEF DESCRIPTION OF THE DRAWINGS

While the specification concludes with claims particularly pointing out and distinctly claiming the subject matter of the present invention, it is believed that the invention can be more readily understood from the following description taken in connection with the accompanying drawings, in which:

DETAILED DESCRIPTION OF THE INVENTION

Figure 1:
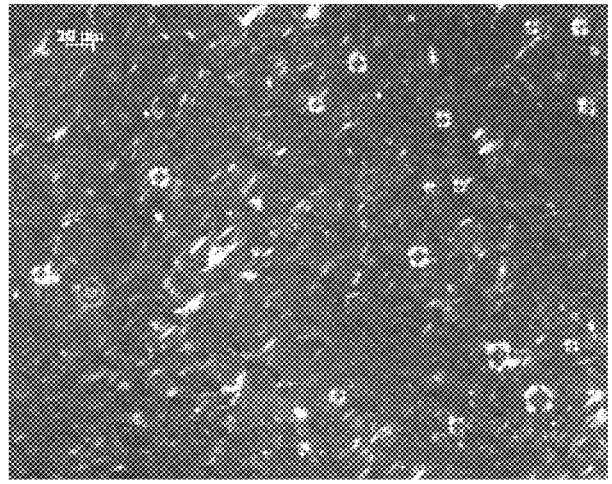
FIG. 1 is a photo taken under microscopy of the gel network structure of Example 1.

Today's hair conditioners almost universally comprise high levels of high melting point fatty compounds, the most common of which are C16 to C18 fatty alcohols. These high melting point fatty compounds are employed as structuring agents when they are combined with one or more surfactants and an aqueous carrier to form a gel network.

The gel network structure can impact the shear stress and conditioning performance, particularly the wet conditioning performance, of the final product. When the gel network structure is in the form of lamella sheets, it can provide excellent conditioning and structure to traditional liquid conditioners.

However, many consumers want a conditioner composition that can be dispensed as a creamy, high-quality foam that can easily be spread throughout their hair. Viscous compositions, such as traditional conditioner products, cannot be dispensed as a high-quality foam by an aerosol dip tube or mechanical pump foamer. It was found that changing the structure of the gel network from all or mostly lamellar sheets to all or mostly vesicles can decrease the viscosity of the conditioner composition (measured and reported as shear stress at a shear rate of 950 $s^{-1}$), allowing the conditioner to be dispensed as a high-quality foam, while still providing consumer acceptable wet conditioning.

It was also found that a uniform gel network or substantially uniform structure can provide improved conditioner compositions that can be dispensed as a creamy, high-quality foam that can easily be spread throughout their hair. The uniformity of a gel network composition can be assessed using the Differential Scanning Calorimetry Method, described herein. If the gel network exhibits one peak (see e.g. Example 2 in FIG. 7), then the gel network is uniform or substantially uniform. If the gel network exhibits more than one peak (see e.g. Comparative Examples A and B in FIG. 7), then the gel network is non-uniform and it may not be consumer acceptable.

The conditioner composition can contain a gel network composition comprising a fatty alcohol and a cationic surfactant with a chloride counterion, such as behenyltrimethylammonium chloride. The gel network in the hair conditioner composition can be mostly vesicles or almost all vesicles. The structure of the gel network can be viewed under a microscope under 40× magnification with polarized light.

The shear stress of the gel network composition (measured at shear stress at $950\ s^{-1}$) can be greater than 50 Pa and less than 200 Pa, which results in a foam with consumer preferred density and compliance. The shear stress of the gel network composition can be impacted by the cooling rate when the composition is made. It was found that cooling the gel network composition too slowly caused the shear stress of the composition to be too low, resulting in a foam that was dispensed as a watery mess.

When the gel network composition is made the components are heated to at least 80° C. The composition can be cooled to ambient temperature with a water bath with a cooling temperature at least 15° C. lower than the composition, alternatively at least 18° C., alternatively at least 20° C., alternatively at least 22° C., and alternatively at least 25° C. The composition can be cooled to ambient temperature with a water bath with a cooling temperature about 15 to about 25° C. lower than the composition, alternatively from about 18 to about 25° C., and alternatively from about 20 to about 25° C.

The conditioner composition can have a liquid phase viscosity of from about 5 cP (5 mPa·s) to about 10,000 cP (10,000 mPa·s), alternatively from about 10 cP (10 mPa·s) to about 9000 cP (9000 mPa·s), alternatively from about 10 cP (10 mPa·s) to about 8000 cP (8000 mPa·s), alternatively from about 20 cP (20 mPa·s) to about 9000 cP (9000 mPa·s), alternatively from about 20 cP (20 mPa·s) to about 8000 cP (8000 mPa·s), alternatively from about 20 cP (20 mPa·s) to about 7000 cP (7000 mPa·s), alternatively from about 20 cP (20 mPa·s) to about 6000 cP (6000 mPa·s), alternatively from about 25 cP (25 mPa·s) to about 5000 cP (5000 mPa·s), alternatively 75 cP (75 mPa·s) to 2000 cP (2000 mPa·s), and alternatively 100 cP (100 mPa·s) to 3000 cP (3000 mPa·s). The hair composition viscosity values may be determined by the Cone/Plate Viscosity Measurement, described hereafter.

The gel network and/or the conditioner can have more than 50% gel network vesicles, alternatively more than 60% vesicles, alternatively more than 70% vesicles, alternatively more than 75% vesicles, alternatively more than 80% vesicles, alternatively more than 85% vesicles, alternatively more than 90% vesicles, and alternatively more than 95% vesicles.

As used herein, the term "fluid" includes liquids and gels.

As used herein, the articles including "a" and "an" when used in a claim, are understood to mean one or more of what is claimed or described.

As used herein, "comprising" means that other steps and other ingredients which do not affect the end result can be added. This term encompasses the terms "consisting of" and "consisting essentially of."

As used herein, "mixtures" is meant to include a simple combination of materials and any compounds that may result from their combination.

As used herein, "molecular weight" or "Molecular weight" refers to the weight average molecular weight unless otherwise stated. Molecular weight is measured using industry standard method, gel permeation chromatography ("GPC").

As used herein, the terms "include," "includes," and "including," are meant to be non-limiting and are understood to mean "comprise," "comprises," and "comprising," respectively.

All percentages, parts and ratios are based upon the total weight of the compositions of the present invention, unless otherwise specified. All such weights as they pertain to listed ingredients are based on the active level and, therefore, do not include carriers or by-products that may be included in commercially available materials.

Unless otherwise noted, all component or composition levels are in reference to the active portion of that component or composition, and are exclusive of impurities, for example, residual solvents or by-products, which may be present in commercially available sources of such components or compositions.

It should be understood that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

For example, if the composition comprises from 1% to 5% fatty alcohol, then a composition comprising 2% stearyl alcohol and 1% cetyl alcohol and no other fatty alcohol, would fall within this scope.

The amount of each particular ingredient or mixtures thereof described hereinafter can account for up to 100% (or 100%) of the total amount of the ingredient(s) in the conditioner composition.

The objects of the present invention are to provide hair conditioner compositions and uses of the compositions as described as described herein for fulfilling the technical effects or goals as set out herein. These objects and other advantages as may be apparent to those skilled in the art can be achieved through the present invention, which is described in the specification and which is defined in the claims which follow.

Gel Network

The gel network composition can be included in conditioner compositions to provide conditioning benefits, in particular improved wet feel of the hair after rinsing the conditioner. As used herein, the term "gel network" refers to a lamellar or vesicular solid crystalline phase which comprises at least one high melting point fatty compound, such as a fatty alcohol, as specified below, at least one surfactant, in particular a cationic surfactant, as specified below, and water or other suitable solvents. The lamellar or vesicular phase comprises bi-layers made up of a first layer comprising the high melting point fatty compound and the surfactant and alternating with a second layer comprising the water or other suitable solvent. Gel networks, generally, are further described by G. M. Eccleston, "Functions of Mixed Emulsifiers and Emulsifying Waxes in Dermatological Lotions and Creams", *Colloids and Surfaces A: Physiochem. and Eng. Aspects* 123-124 (1997) 169-182; and by G. M Eccleston, "The Microstructure of Semisolid Creams", *Pharmacy International, Vol.* 7, 63-70 (1986).

The conditioner composition can have a total gel network mole content from about 0.1 to about 0.5 mol/100 g, alternatively from about 0.13 to about 0.45 mol/100 g, alternatively from about 0.15 to about 0.4 mol/100 g, alternatively from about 0.17 to about 0.37 mol/100 g, alternatively from about 0.18 to about 0.35 mol/100 g, alternatively from about 0.20 to about 0.32 mol/100 g, and alternatively from about 0.21 to about 0.3 mol/100 g. The conditioner composition can have a total gel network mole content from about 0.1 to about 0.5 mol/100 g, alternatively from about 0.13 to about 0.45 mol/100 g, alternatively from about 0.15 to about 0.4 mol/100 g, alternatively from about 0.17 to about 0.37 mol/100 g, alternatively from about 0.18 to about 0.35 mol/100 g, alternatively from about 0.20 to about 0.32 mol/100 g, and alternatively from about 0.21 to about 0.3 mol/100 g, wherein the Total gel network mole content is calculated as the sum of the moles of the fatty alcohols and the moles of the cationic surfactant(s).

The mole ratio of cationic surfactant to fatty alcohol can be from about 0.55 to about 1.2, alternatively from about 0.6 to about 1.15, from about 0.63 to about 1.1, alternatively from about 0.65 to about 1.05, and alternatively from about 0.66 to about 1.

The mole ratio of cationic surfactant to total gel network can be greater than 35 and less than 55, alternatively from about 36 to about 54, alternatively from about 38 to about 52, and alternatively from about 40 to about 50.

The mole ratio of fatty alcohol to total gel network can be from about 40 to about 70, alternatively from about 45 to about 65, and alternatively from about 40 to about 60.

The mole ratio of C18 fatty alcohol to total fatty alcohol is from 60 to about 80, alternatively from about 65 to about 75, and alternatively from about 67 to about 73.

The mole ratio of C16 fatty alcohol to total fatty alcohol is from about 20 to about 40, alternatively from about 25 to about 35, and alternatively from about 27 to about 33.

The conditioner composition can be dispensed as a foam from a pump or an aerosol mechanical pump foamer. The viscosity and shear stress of the foam can significantly impact the foam quality and these factors are influenced by the shear stress of the gel network base composition. If the shear stress of the gel network base composition is less than 50 Pa, the foam can be too compliant and can be dispensed as a sloppy mess, making it nearly impossible to efficiently distribute through a user's hair. The shear stress of the gel network composition can be greater than 50 and less than 200 Pa. The shear stress of the gel network composition can be from about 55 Pa to about 260 Pa, alternatively from about 60 Pa to about 225 Pa, alternatively from about 60 Pa to about 200 Pa, alternatively from about 65 Pa to about 195 Pa, and alternatively from about 67 Pa to about 190 Pa. The shear stress can be determined using the Shear Stress Test Method, described hereafter.

Cationic Surfactant

The conditioner composition can contain from about 1 wt. % to about 10 wt. %, alternatively from about 1.5 wt. % to about 8 wt. %, alternatively from about 1.8 wt. % to about 7 wt. %, alternatively from about 2 wt. % to about 6.5 wt. %, alternatively from about 2.5 wt. % to about 6 wt. %, alternatively from about 3 wt. % to about 5.5 wt. %, and alternatively from about 3.5 wt. % to about 5 wt. % cationic surfactant.

The cationic surfactant can a cationic surfactant having a chloride counterion, including but not limited to behenyltrimethylammonium chloride, cetyl trimethyl ammonium chloride, stearyl trimethyl ammonium chloride, ditallow alkyl dimethyl ammonium chloride, dihydrogenated tallow alkyl dimethyl ammonium chloride, distearyl dimethyl ammonium chloride, dicetyl dimethyl ammonium chloride, and combinations thereof. The cationic surfactant can be behenyltrimethylammonium chloride.

Cationic surfactants useful herein are mono-alkyl quaternized ammonium cationic surfactants having one long alkyl chain with from about 12 to about 40 carbon atoms preferably from about 16 to about 30 carbon atoms, neutralized with HCl, thus, with Cl counterion. Preferred mono-alkyl quaternized ammonium cationic surfactants are behenyltrimethylammonium chloride, cetyltrimethyl ammonium chloride, stearyl trimethyl ammonium chloride.

The conditioner composition can contain other cationic surfactants such as other mono-long alkyl cationic surfactants having one long alkyl chain with from about 12 to about 40 carbon atoms preferably from about 16 to about 30 carbon atoms. Such other mono-long alkyl cationic surfactants, include, for example: other mono-long alkyl quaternized ammonium salts such as behenyl trimethyl ammonium methosulfate, cetyl trimethyl ammonium chloride, stearyl trimethyl ammonium chloride; tertiary amines, tertiary amidoamines and salts thereof such as a salt of stearylamidopropyl dimethyamine and 1-glutamic acid, and a salt of behenylamidopropyl dimethyamine and 1-glutamic acid.

The conditioner composition can contain other cationic surfactants such as tertiary amidoamines having an alkyl group of from about 12 to about 22 carbon atoms, preferably from about 16 to about 22 carbon atoms. Exemplary tertiary amido amines include: stearamidopropyldimethylamine, stearamidopropyldiethylamine, stearamidoethyldiethylamine, stearamidoethyldimethylamine, palmitamidopropyldimethylamine, palmitamidopropyldiethylamine, palmitamidoethyldiethylamine, palmitamidoethyldimethylamine, behenamidopropyldimethylamine, behenamidopropyldiethylamine, behenamidoethyldiethylamine, behenamidoethyldimethylamine, arachidamidopropyldimethylamine, arachidamidopropyldiethyl amine, arachidamidoethyldiethylamine, arachidamidoethyldimethylamine, diethylaminoethylstearamide.

Useful amines in the present invention are disclosed in U.S. Pat. No. 4,275,055, Nachtigal, et al. The above mono-alkyl amine cationic surfactants are preferably used in combination with acids such as l-glutamic acid, lactic acid, hydrochloric acid, malic acid, succinic acid, acetic acid, fumaric acid, tartaric acid, citric acid, l-glutamic hydrochloride, maleic acid, and mixtures thereof; more preferably l-glutamic acid, lactic acid, citric acid. The acid can be used at a molar ratio of the amine to the acid of from about 1:0.3 to about 1:2, more preferably from about 1:0.4 to about 1:1.

The composition of the present invention may contain a di-alkyl quaternized ammonium salt cationic surfactant. The di-alkyl quaternized ammonium salt cationic surfactants useful herein are those having two long alkyl chains of from 12 to 30 carbon atoms, more preferably from 16 to 24 carbon atoms, still more preferably from 18 to 22 carbon atoms. Such di-alkyl quaternized ammonium salts useful herein are those having the formula (I):

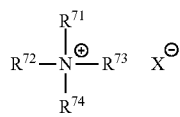
(I)

wherein two of $R^{71}$, $R^{72}$, $R^{73}$ and $R^{74}$ are selected from an aliphatic group of from 12 to 30 carbon atoms, preferably from 16 to 24 carbon atoms, more preferably from 18 to 22 carbon atoms or an aromatic, alkoxy, polyoxyalkylene, alkylamido, hydroxyalkyl, aryl or alkylaryl group having up to about 30 carbon atoms; the remainder of $R^{71}$, $R^{72}$, $R^{73}$ and $R^{74}$ are independently selected from an aliphatic group of from 1 to about 8 carbon atoms, preferably from 1 to 3 carbon atoms or an aromatic, alkoxy, polyoxyalkylene, alkylamido, hydroxyalkyl, aryl or alkylaryl group having up to about 8 carbon atoms; and $X^-$ is a salt-forming anion selected from the group consisting of halides such as chloride and bromide, C1-C4 alkyl sulfate such as methosulfate and ethosulfate, and mixtures thereof. The aliphatic groups can contain, in addition to carbon and hydrogen atoms, ether linkages, and other groups such as amino groups. The longer chain aliphatic groups, e.g., those of about 16 carbons, or higher, can be saturated or unsaturated. Preferably, two of $R^{71}$, $R^{72}$, $R^{73}$ and $R^{74}$ are selected from an alkyl group of from 12 to 30 carbon atoms, preferably from 16 to 24 carbon atoms, more preferably from 18 to 22 carbon atoms; and the remainder of $R^{71}$, $R^{72}$, $R^{73}$ and $R^{74}$ are independently selected from $CH_3$, $C_2H_5$, $C_2H_4OH$, $CH_2C_6H_5$, and mixtures thereof.

Such preferred di-alkyl cationic surfactants include, for example, dialkyl (14-18) dimethyl ammonium chloride, ditallow alkyl dimethyl ammonium chloride, dihydrogenated tallow alkyl dimethyl ammonium chloride, distearyl dimethyl ammonium chloride, and dicetyl dimethyl ammonium chloride.

When other cationic surfactants are contained, the behenyltrimethylammonium chloride can be included at a level of from about 50% to about 100%, alternatively from about 70% to about 100%, alternatively from about 80% to about 100%, alternatively from about 90% to about 100%, by weight of the total amount of the cationic surfactants in the composition. Additional cationic surfactants that may be suitable for the conditioner composition are found in U.S. Pat. No. 9,993,419, incorporated by reference.

High Melting Point Fatty Compounds

The conditioner composition can contain from about 1 wt. % to about 10 wt. %, alternatively from about 1.5 wt. % to about 9 wt. %, alternatively from about 2 wt. % to about 8.5 wt. %, alternatively from about 1.5 wt. % to about 8 wt. %, alternatively from about 2 wt. % to about 7 wt. %, alternatively from about 2.5 wt. % to about 6 wt. %, alternatively from about 2.5 wt. % to about 5 wt. %, and alternatively from about 2.5 wt. % to about 4.5 wt. % high melting point fatty compound.

The high melting point fatty compounds can have a melting point of about 25° C. or higher and can be selected from the group consisting of fatty alcohols, fatty acids, fatty alcohol derivatives, fatty acid derivatives, and mixtures thereof. It is understood by the artisan that the compounds disclosed in this section of the specification can in some instances fall into more than one classification, e.g., some fatty alcohol derivatives can also be classified as fatty acid derivatives. However, a given classification is not intended to be a limitation on that particular compound but is done so for convenience of classification and nomenclature. Further, it is understood by the artisan that, depending on the number and position of double bonds, and length and position of the branches, certain compounds having certain required carbon atoms may have a melting point of less than about 25° C. Such compounds of low melting point are not intended to be included in this section. Nonlimiting examples of the high melting point compounds are found in *International Cosmetic Ingredient Dictionary*, Fifth Edition, 1993, *and CTFA Cosmetic Ingredient Handbook*, Second Edition, 1992.

The fatty alcohols described herein are those having from about 14 to about 30 carbon atoms, preferably from about 16 to about 22 carbon atoms. These fatty alcohols are saturated and can be straight or branched chain alcohols. Nonlimiting examples of fatty alcohols include cetyl alcohol, stearyl alcohol, behenyl alcohol, and mixtures thereof.

The fatty acids useful herein are those having from about 10 to about 30 carbon atoms, preferably from about 12 to about 22 carbon atoms, and more preferably from about 16 to about 22 carbon atoms. These fatty acids are saturated and can be straight or branched chain acids. Also included are diacids, triacids, and other multiple acids which meet the requirements herein. Also included herein are salts of these fatty acids. Nonlimiting examples of fatty acids include lauric acid, palmitic acid, stearic acid, behenic acid, sebacic acid, and mixtures thereof.

The fatty alcohol derivatives and fatty acid derivatives useful herein include alkyl ethers of fatty alcohols, alkoxylated fatty alcohols, alkyl ethers of alkoxylated fatty alcohols, esters of fatty alcohols, fatty acid esters of compounds having esterifiable hydroxy groups, hydroxy-substituted fatty acids, and mixtures thereof. Nonlimiting examples of fatty alcohol derivatives and fatty acid derivatives include materials such as methyl stearyl ether; the ceteth series of compounds such as ceteth-1 through ceteth-45, which are ethylene glycol ethers of cetyl alcohol, wherein the numeric designation indicates the number of ethylene glycol moieties present; the steareth series of compounds such as steareth-1 through steareth-10, which are ethylene glycol ethers of steareth alcohol, wherein the numeric designation indicates the number of ethylene glycol moieties present; ceteareth 1 through ceteareth-10, which are the ethylene glycol ethers of ceteareth alcohol, i.e., a mixture of fatty alcohols containing predominantly cetyl and stearyl alcohol, wherein the numeric designation indicates the number of ethylene glycol moieties present; C16-C30 alkyl ethers of the ceteth, steareth, and ceteareth compounds just described; polyoxyethylene ethers of behenyl alcohol; ethyl stearate, cetyl stearate, cetyl palmitate, stearyl stearate, myristyl myristate, polyoxyethylene cetyl ether stearate, polyoxyethylene stearyl ether stearate, polyoxyethylene lauryl ether stearate, ethyleneglycol monostearate, polyoxyethylene monostearate, polyoxyethylene distearate, propyleneglycol monostearate, propyleneglycol distearate, trimethylolpropane distearate, sorbitan stearate, polyglyceryl stearate, glyceryl monostearate, glyceryl distearate, glyceryl tristearate, and mixtures thereof.

The fatty compound may be a single high melting point compound of high purity. Single compounds of pure fatty alcohols selected may be selected from the group consisting of pure cetyl alcohol, stearyl alcohol, and behenyl alcohol. By "pure" herein, what is meant is that the compound has a purity of at least about 90%, alternatively at least about 95%.

Commercially available high melting point fatty compounds described herein include: cetyl alcohol, stearyl alcohol, and behenyl alcohol having tradenames KONOL series available from Shin Nihon Rika (Osaka, Japan), and NAA series available from NOF (Tokyo, Japan); pure behenyl alcohol having tradename 1-DOCOSANOL available from WAKO (Osaka, Japan), various fatty acids having tradenames NEO-FAT available from Akzo (Chicago, Ill. USA), HYSTRENE available from Witco Corp. (Dublin, Ohio USA), and DERMA available from Vevy (Genova, Italy).

Oils for Hair Conditioning

The conditioner composition can contain one or more oils for conditioning the hair. It is believed that the oils can provide smoothness and softness on dry hair. The conditioner composition may comprise from about 0.5% to about 8%, alternatively from about 1% to about 6%, alternatively from about 1.5% to about 5%, and alternatively from about 2% to about 4% of one or more oils, by weight of the conditioner composition. The particle size of the one or more oils may be from about 1 nm to about 500 nm, alternatively from about 5 nm to about 250 nm, alternatively from about 10 nm to about 100 nm, and alternatively from about 12 nm to about 50 nm. The oils described herein are silicone-free.

The particle size of the one or more oils can be measured by dynamic light scattering (DLS) using the measurement angle and the refractive index of the one or more oils. A Malvern Zetasizer Nano ZEN3600 system using He-Ne laser 633 nm can be used for the measurement at 25° C.

The Zetasizer Software provided by Malvern Instruments, was used for data analysis. For each sample, 3 measurements were made and Z-average values were reported as the particle size.

In an embodiment, the one or more oils may be in the form of a nanoemulsion. The nanoemulsion may comprise any oil suitable for application to the skin and/or hair.

Non-limiting examples of oils can be selected from the group consisting of silicones, natural oils, and combinations thereof.

Silicone

The silicone compounds can have an average particle size of from 1 micron to about 50 microns. Alternatively, the one or more silicones may be in the form of a nanoemulsion.

The conditioner composition can contain polyalkyl siloxanes include, for example, polydimethylsiloxane, polydiethylsiloxane, and polymethylphenylsiloxane. In one example, the composition can contain polydimethylsiloxane, which is also known as dimethicone. These silicone compounds are available, for example, from the General Electric® Company in their Viscasil® and TSF 451 series, and from Dow Corning in their Dow Corning® SH200 series.

The silicone compounds useful herein also include a silicone gum. The term "silicone gum", as used herein, means a polyorganosiloxane material having a viscosity at 25° C. of greater than or equal to 1,000,000 centistokes. It is recognized that the silicone gums described herein can also have some overlap with the above-disclosed silicone compounds. This overlap is not intended as a limitation on any of these materials. The "silicone gums" will typically have a mass molecular weight in excess of about 200,000, generally between about 200,000 and about 1,000,000. Specific examples include polydimethylsiloxane, poly(dimethylsiloxane methylvinylsiloxane) copolymer, poly(dimethylsiloxane diphenylsiloxane methylvinylsiloxane) copolymer and mixtures thereof. The silicone gums are available, for example, as a mixture with silicone compounds having a lower viscosity. Such mixtures useful herein include, for example, Gum/Cyclomethicone blend available from Shin-Etsu.

The one or more silicones can include one or more aminosilicones corresponding to formula (I):

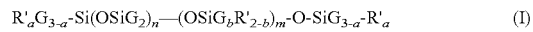

$$R'_aG_{3-a}\text{-Si}(OSiG_2)_n\text{---}(OSiG_bR'_{2-b})_m\text{-O-SiG}_{3-a}\text{-R'}_a \qquad (I)$$

in which:

G is chosen from a hydrogen atom, a phenyl group, OH group, and $C_1$-$C_8$ alkyl groups, for example methyl,
a is an integer ranging from 0 to 3, and alternatively a is 0,
b is chosen from 0 and 1, and alternatively b is 1,
m and n are numbers such that the sum (n+m) can range for example from 1 to 2 000, such as for example from 50 to 150, wherein n can be for example chosen from numbers ranging from 0 to 1 999, such as for example from 49 to 149, and wherein m can be chosen from numbers ranging for example from 1 to 2 000, such as for example from 1 to 10;
R' is a monovalent group of formula —$C_qH_{2q}$L in which q is a number from 2 to 8 and L is an optionally quaternized amine group chosen from the groups:
—NR"—$CH_2$—$CH_2$—N'($R^1$)$_2$,
—N(R")$_2$,
—$N^+$(R")$_3$A$^-$,
—$N^+$H(R")$_2$A$^-$,
—$N^+$H$_2$(R")A$^-$, and
—N(R")—$CH_2$—$CH_2$—$N^+$R"H$_2$A$^-$, in which R" can be chosen from a hydrogen atom, phenyl groups, benzyl groups, and saturated monovalent hydrocarbon-based groups, such as for example an alkyl group comprising from 1 to 20 carbon atoms, and A$^-$ is chosen from halide ions such as, for example, fluoride, chloride, bromide and iodide.

In one example, the amino silicone can correspond to formula (I) wherein m=0, a=1, q=3, G=methyl, n is from about 1500 to about 1700, alternatively about 1600; and L is —N(CH$_3$)$_2$ or —NH$_2$.

In another example, the amino silicones can correspond to formula (I) wherein m=0, a=1, q=3, G=methyl, n is from about 400 to about 600, alternatively about 500; and L is —N(CH$_3$)$_2$ or —NH$_2$. This amino silicones can be called as terminal aminosilicones, as one or both ends of the silicone chain are terminated by nitrogen containing group.

The above aminosilicones, when incorporated into the composition, can be mixed with solvent having a lower viscosity.

The above aminosilicones, when incorporated into the composition, can be mixed with solvent having a lower viscosity. Such solvents can include, for example, polar or non-polar, volatile or non-volatile oils. Such oils can include, for example, silicone oils, hydrocarbons, and esters. Among such a variety of solvents, preferred are those selected from the group consisting of non-polar, volatile hydrocarbons, volatile cyclic silicones, non-volatile linear silicones, and mixtures thereof. The non-volatile linear silicones useful herein are those having a viscosity of from about 1 to about 20,000 centistokes, preferably from about 20 to about 10,000 centistokes at 25° C. Among the preferred solvents, highly preferred are non-polar, volatile hydrocarbons, especially non-polar, volatile isoparaffins, in view of reducing the viscosity of the aminosilicones and providing improved hair conditioning benefits such as reduced friction on dry hair. Such mixtures have a viscosity of preferably from about 1,000 mPa·s to about 100,000 mPa·s, more preferably from about 5,000 mPa·s to about 50,000 mPa·s.

Other suitable alkylamino substituted silicone compounds include those having alkylamino substitutions as pendant groups of a silicone backbone. In one example, the silicone contains "amodimethicone". Commercially available amodimethicones useful herein include, for example, BY16-872 available from Dow Corning®.

In one example, the silicone can be aminopropyl terminated polydimethylsiloxane, corresponding to structure (II) below, (where n is a integer). The molecular weight may be from about 5,000 to about 70,000, alternatively from about 8,000 to 15,000.

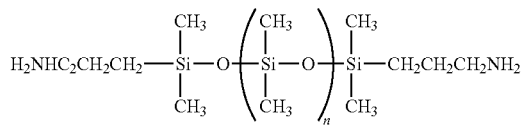

(II)

In another example, the composition may contain polyorganosiloxane compound comprising: one or more quaternary ammonium groups; silicone blocks comprising between about 99 and about 199 siloxane units on average; at least one polyalkylene oxide structural unit; and at least one terminal ester group. An example of this type of siloxane polymer is silicone quaternium-26, which is formed by the reaction between glycidoxy-terminated polydimethylsiloxane, N,N,N',N'-tetramethyl-1,6-hexanediamine, PPG-3 and Lauric Acid.

Additional, non-limiting examples of silicones can be found in U.S. Pub. Nos. 2009/0324529 and 2018/0168948, incorporated by reference.

Natural Oils

Natural Oils can include glycerides, acetoglyceride esters, alkyl esters, alkenyl esters, polyglycerin fatty acid esters, lanolin and lanolin derivatives, milk triglycerides (e.g., hydroxylated milk glyceride) and polyol fatty acid polyesters, wax esters, and combinations thereof.

Non-limiting examples glycerides can include castor oil, soy bean oil, derivatized soybean oils such as maleated soy bean oil, safflower oil, cotton seed oil, corn oil, walnut oil, peanut oil, olive oil, cod liver oil, almond oil, avocado oil, palm oil and sesame oil, vegetable oils, sunflower seed oil, and vegetable oil derivatives; coconut oil and derivatized coconut oil, cottonseed oil and derivatized cottonseed oil, jojoba oil, cocoa butter, and combinations thereof.

Non-limiting examples of acetoglyceride esters can include acetylated monoglycerides.

Non-limiting examples of alkyl esters can include isopropyl esters of fatty acids and long chain esters of long chain (i.e. C10-C24) fatty acids, e.g. cetyl ricinoleate, non-limiting examples of which incloude isopropyl palmitate, isopropyl myristate, cetyl riconoleate and stearyl riconoleate. Other examples are: hexyl laurate, isohexyl laurate, myristyl myristate, isohexyl palmitate, decyl oleate, isodecyl oleate, hexadecyl stearate, decyl stearate, isopropyl isostearate, diisopropyl adipate, diisohexyl adipate, dihexyldecyl adipate, diisopropyl sebacate, acyl isononanoate lauryl lactate, myristyl lactate, cetyl lactate, and combinations thereof.

Non-limiting examples of alkenyl esters can include oleyl myristate, oleyl stearate, oleyl oleate, and combinations thereof.

Non-limiting examples of polyglycerin fatty acid esters suitable for use as hair conditioning agents herein can include decaglyceryl distearate, decaglyceryl diisostearate, decaglyceryl monomyriate, decaglyceryl monolaurate, hexaglyceryl monooleate, and combinations thereof.

Non-limiting examples of lanolin and lanolin derivatives suitable for use as hair conditioning agents herein can include lanolin, lanolin oil, lanolin wax, lanolin alcohols, lanolin fatty acids, isopropyl lanolate, acetylated lanolin, acetylated lanolin alcohols, lanolin alcohol linoleate, lanolin alcohol riconoleate, and combinations thereof.

Still other suitable hair conditioning agents include wax esters, non-limiting examples of which include beeswax and beeswax derivatives, spermaceti, myristyl myristate, stearyl stearate, and combinations thereof. Also useful are vegetable waxes such as carnauba and candelilla waxes;

sterols such as cholesterol, cholesterol fatty acid esters; and phospholipids such as lecithin and derivatives, sphingo lipids, ceramides, glycosphingo lipids, and combinations thereof. Also suitable benefit agents include glycerol monooleate.

In some examples, the oil can include castor oil, soy bean oil, derivatized soybean oils such as maleated soy bean oil, safflower oil, cotton seed oil, corn oil, walnut oil, peanut oil, olive oil, cod liver oil, almond oil, avocado oil, palm oil and sesame oil, vegetable oils, sunflower seed oil, and vegetable oil derivatives; coconut oil and derivatized coconut oil, cottonseed oil and derivatized cottonseed oil, jojoba oil, cocoa butter, and combinations thereof.

In other examples the oil can include soy bean oil, derivatized soybean oils such as maleated soy bean oil, safflower oil, and combinations thereof.

Additional natural oils can be found in U.S. Pub. No. 2017/0165156 and App. No. 62/715,949, incorporated by reference.

Other Ingredients

Rheology Modifier

The conditioner composition may include one or more rheology modifiers to adjust the rheological characteristics of the composition for better feel, in-use properties and the suspending stability of the composition. For example, the rheological properties can be adjusted so that the composition remains uniform during its storage and transportation and it does not drip undesirably onto other areas of the body, clothing or home furnishings during its use. Any suitable rheology modifier can be used. In the present invention, the leave-on treatment may comprise from about 0.01% to about 3% of a rheology modifier, alternatively from about 0.1% to about 1% of a rheology modifier.

The one or more rheology modifier may be selected from the group consisting of polyacrylamide thickeners, cationically modified polysaccharides, associative thickeners, and mixtures thereof. Associative thickeners include a variety of material classes such as, for example: hydrophobically modified cellulose derivatives; hydrophobically modified alkoxylated urethane polymers, such as PEG-150/decyl alcohol/SMDI copolymer, PEG-150/stearyl alcohol/SMDI copolymer, polyurethane-39; hydrophobically modified, alkali swellable emulsions, such as hydrophobically modified polypolyacrylates, hydrophobically modified polyacrylic acids, and hydrophobically modified polyacrylamides; hydrophobically modified polyethers. These materials may have a hydrophobe that can be selected from cetyl, stearyl, oleayl, and combinations thereof, and a hydrophilic portion of repeating ethylene oxide groups with repeat units from 10-300, alternatively from 30-200, and alternatively from 40-150. Examples of this class include PEG-120-methylglucose dioleate, PEG-(40 or 60) sorbitan tetraoleate, PEG-150 pentaerythrityl tetrastearate, PEG-55 propylene glycol oleate, PEG-150 distearate.

Non-limiting examples of additional rheology modifiers include acrylamide/ammonium acrylate copolymer (and)

polyisobutene (and) polysorbate 20; acrylamide/sodium acryloyldimethyl taurate copolymer/isohexadecane/polysorbate 80; acrylates copolymer; acrylates/beheneth-25 methacrylate copolymer; acrylates/C10-C30 alkyl acrylate crosspolymer; acrylates/steareth-20 itaconate copolymer; ammonium polyacrylate/Isohexadecane/PEG-40 castor oil; C12-16 alkyl PEG-2 hydroxypropylhydroxyethyl ethylcellulose (HM-EHEC); carbomer; crosslinked polyvinylpyrrolidone (PVP); dibenzylidene sorbitol; hydroxyethyl ethylcellulose (EHEC); hydroxypropyl methylcellulose (HPMC); hydroxypropyl methylcellulose (HPMC); hydroxypropylcellulose (HPC); methylcellulose (MC); methylhydroxyethyl cellulose (MEHEC); PEG-150/decyl alcohol/SMDI copolymer; PEG-150/stearyl alcohol/SMDI copolymer; polyacrylamide/C13-14 isoparaffin/laureth-7; polyacrylate 13/polyisobutene/polysorbate 20; polyacrylate crosspolymer-6; polyamide-3; polyquaternium-37 (and) hydrogenated polydecene (and) trideceth-6; polyurethane-39; sodium acrylate/acryloyldimethyltaurate/dimethylacrylamide; crosspolymer (and) isohexadecane (and) polysorbate 60; sodium polyacrylate. Exemplary commercially-available rheology modifiers include ACULYN™ 28, Klucel M CS, Klucel H CS, Klucel G CS, SYLVACLEAR AF1900V, SYLVACLEAR PA1200V, Benecel E10M, Benecel K35M, Optasense RMC70, ACULYN™33, ACULYN™46, ACULYN™22, ACULYN™44, Carbopol Ultrez 20, Carbopol Ultrez 21, Carbopol Ultrez 10, Carbopol 1342, Sepigel™305, Simulge™600, Sepimax Zen, Cosmedia Ultragel 300, Polysurf 67CS, Natrosol plus 330CS and/or combinations thereof.

Perfume

The hair conditioner composition may contain from about 0.25% to about 5%, alternatively from about 0.5% to about 4%, alternatively from about 0.5% to about 3%, and alternatively from about 1% to about 3% perfume, by weight of the composition. In another example, the conditioner composition may contain from about 0.75% to about 7%, alternatively from about 1% to about 6%, alternatively from about 1.5% to about 5%, alternatively from about 1.25% to about 4% perfume, and alternatively from about 2% to about 3.5% perfume, by weight of the conditioner composition.

Examples of suitable perfumes may be provided in the CTFA (Cosmetic, Toiletry and Fragrance Association) 1992 International Buyers Guide, published by CFTA Publications and OPD 1993 Chemicals Buyers Directory 80th Annual Edition, published by Schnell Publishing Co. A plurality of perfume components may be present in the conditioner composition and the pressurized conditioner composition.

Water

The conditioner composition may contain from about from about 60% to about 90% water, alternatively from about 65% to about 87.5%, alternatively from about 67.5% to about 85%, alternatively from about 70% to about 82.5%, and alternatively from about 72.5% to about 80% water.

Additional Components

The composition of the present invention may include other additional components, which may be selected by the artisan according to the desired characteristics of the final product and which are suitable for rendering the composition more cosmetically or aesthetically acceptable or to provide them with additional usage benefits. Such other additional components generally are used individually at levels of from about 0.001% to about 10%, preferably up to about 5% by weight of the composition.

A wide variety of other additional components can be formulated into the present compositions. These include: other conditioning agents such as hydrolysed collagen with tradename Peptein 2000 available from Hormel, vitamin E with tradename Emix-d available from Eisai, panthenol available from Roche, niacinamide, treahalose, panthenyl ethyl ether available from Roche, hydrolysed keratin, proteins, plant extracts, and nutrients; preservatives such as benzyl alcohol, methyl paraben, propyl paraben and imidazolidinyl urea; pH adjusting agents, such as citric acid, sodium citrate, succinic acid, phosphoric acid, sodium hydroxide, sodium carbonate; coloring agents, such as any of the FD&C or D&C dyes; and sequestering agents, such as disodium ethylenediamine tetra-acetate; ultraviolet and infrared screening and absorbing agents such as benzophenones; and antidandruff agents such as zinc pyrithione, salicylic acid, sulfur, coal tar, selenium disulfide, ketoconazole, and/or piroctone olamine Propellant The conditioner composition described herein may comprise from about from about 2% to about 10% propellant, alternatively from about 3% to about 8% propellant, and alternatively from about 4% to about 7% propellant, by weight of the conditioner.

The propellant may comprise one or more volatile materials, which in a gaseous state, may carry the other components of the conditioner in particulate or droplet form. The propellant may have a boiling point within the range of from about −45° C. to about 5° C. The propellant may be liquefied when packaged in convention aerosol containers under pressure. The rapid boiling of the propellant upon leaving the aerosol foam dispenser may aid in the atomization of the other components of the conditioner composition.

Aerosol propellants which may be employed in the aerosol composition may include the chemically-inert hydrocarbons such as propane, n-butane, isobutane, cyclopropane, and mixtures thereof, as well as halogenated hydrocarbons such as dichlorodifluoromethane, 1,1-dichloro-1,1,2,2-tetrafluoroethane, 1-chloro-1,1-difluoro-2,2-trifluoroethane, 1-chloro-1,1-difluoroethylene, 1,1-difluoroethane, dimethyl ether, monochlorodifluoromethane, trans-1,3,3,3-tetrafluoropropene (HFO 1234ze available by Honeywell), and mixtures thereof. The propellant may comprise hydrocarbons such as isobutane, propane, and butane—these materials may be used for their low ozone reactivity and may be used as individual components where their vapor pressures at 21.1° C. range from about 1.17 Bar to about 7.45 Bar, alternatively from about 1.17 Bar to about 4.83 Bar, and alternatively from about 2.14 Bar to about 3.79 Bar. The propellant may comprise hydrofluoroolefins (HFOs).

Compositions that use an HFO propellant can have higher foam densities (approximately 2× greater) versus hydrocarbon propellants and at equal formula pressure and formula % saturated pressure. The higher density can enable higher gravimetric foam dosage per unit volume of the resulting dispensed foam conditioner. This means that a consumer could use a smaller volume of foam to achieve similar results when using a less dense foam.

The pressure and % saturated pressure can be important to enable sufficient foam dispensing over the life of the product (from beginning to middle to end of the pressurized container). The 1,3,3,3-tetrafluoropropene can also enable significantly greater gloss or shine of the dispensed foam.

Packaging

The conditioner composition can be stored and dispensed from a foaming dispenser including aerosol foamers or mechanical pump foamers.

Aerosol Foamer

Figure 5:
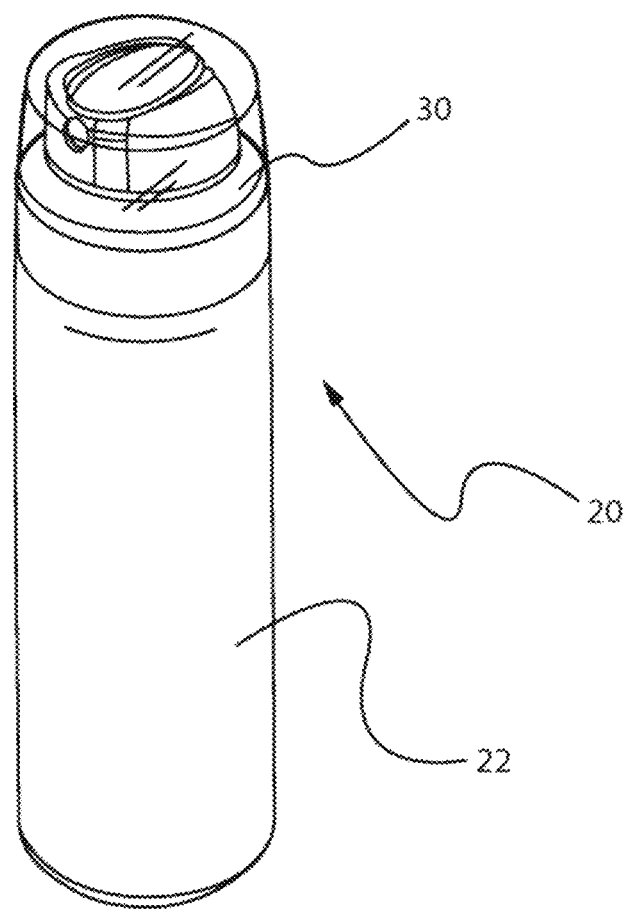
FIG. 5 is a perspective view of an aerosol dispenser according to the present invention having a plastic outer container and a bag.
Figures 6A, 6B:
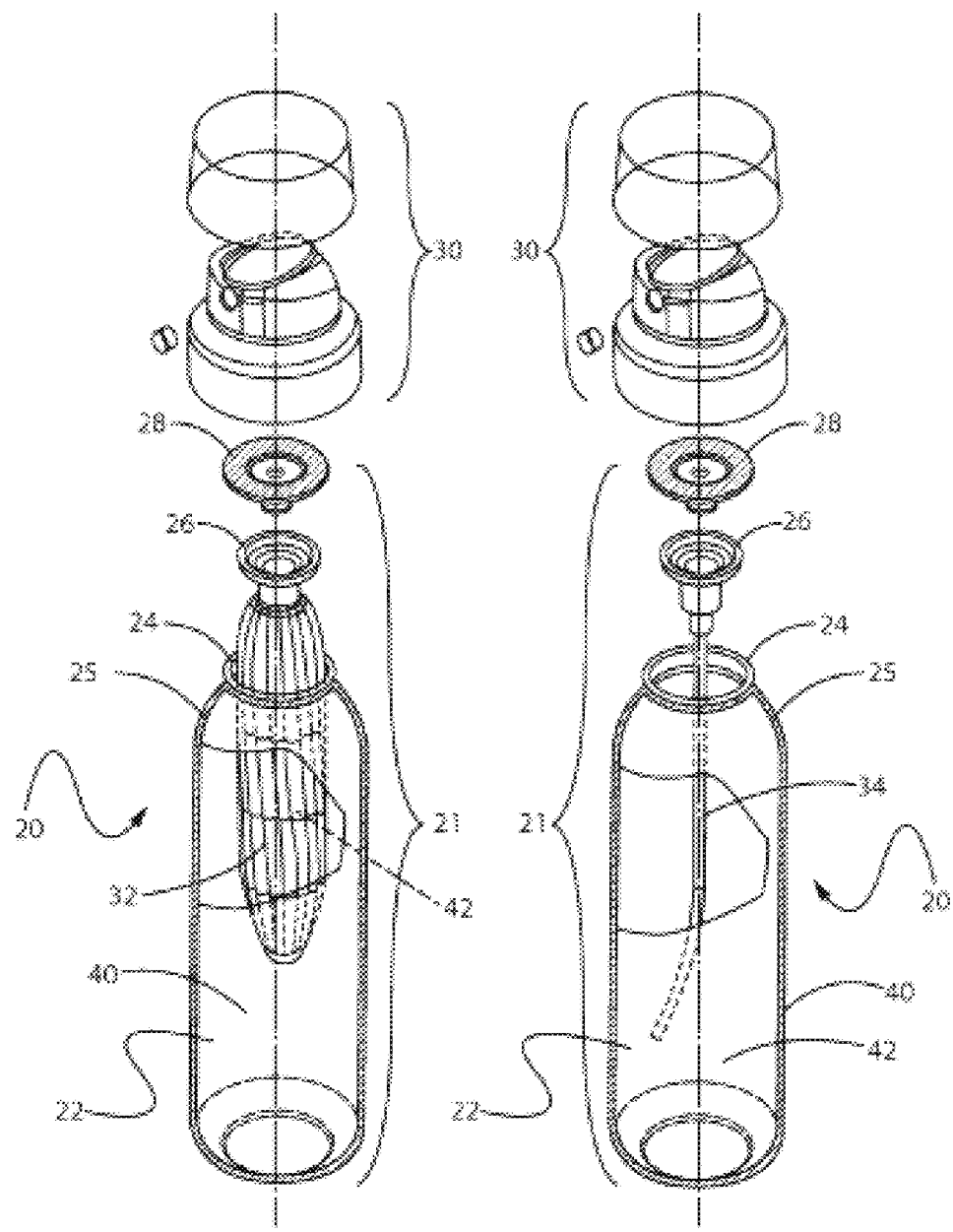
FIG. 6A is an exploded perspective view of the aerosol dispenser of FIG. 5 having a collapsible bag.
FIG. 6B is an exploded perspective view of the aerosol dispenser of FIG. 1 having a dip tube.

Referring to FIGS. 5, 6A, and 6B, an aerosol dispenser 20 is shown. The dispenser 20 comprises a pressurizeable outer container 22. The outer container 22 can comprise any suitable material, including plastic or metal. The outer container 22 may have an opening. The opening defines a neck 24, to which other components may be sealed. The neck 24 may be connected to the container sidewall by a shoulder 25.

Referring to FIGS. 6A and 6B, a valve cup 26 may be sealed to the opening of the outer container 22. The seal, outer container and other container components can be selected to be resistant to the conditioner composition 42 and/or propellant 40.

A valve assembly 28, in turn, may be disposed within the valve cup 26. The valve assembly 28 provides for retention of conditioner composition 42 within the aerosol dispenser 20 until the conditioner composition 42 is selectively dispensed by a user. The valve assembly 28 may be selectively actuated by an actuator 30. Selective actuation of the valve assembly 28 allows the user to dispense a desired quantity of the conditioner composition 42 on demand. The conditioner composition can be dispensed as a foam.

Figure 4:
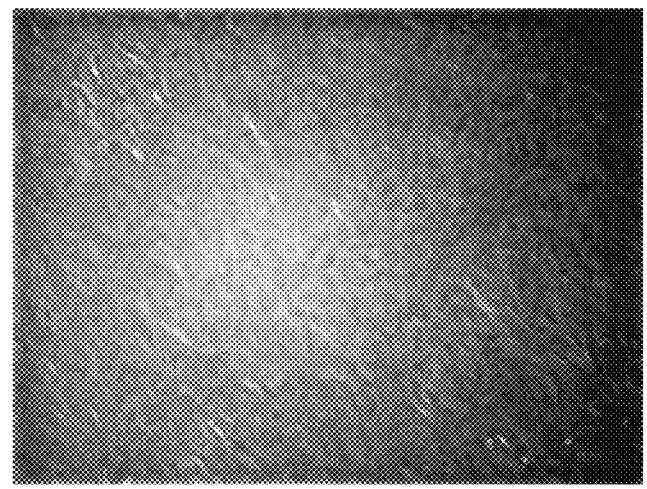
FIG. 4 is a photo taken under microscopy of the gel network structure of Comparative Example B.

Inside the outer container 22 may be a product delivery device. The product delivery device may comprise a collapsible bag 32 which can be made of gas impermeable material as shown in FIG. 4A. The collapsible bag 32 may be mounted in a sealing relationship to the neck 24 of the container (i.e. a bag-on-can arrangement). Alternative the collapsible bag 32 may be mounted in sealing relationship to the valve assembly 28 (i.e. a bag-on-valve arrangement).

The collapsible bag 32 may hold conditioner composition 42 therein and prevent intermixing of such conditioner composition 42 with propellant 40, which can also be referred to as driving gas. The propellant 40 may be stored outside the collapsible bag 32, and inside the outer container 22. The propellant may be any gas as long as it does not excessively penetrate the walls of the collapsible bag 32 or outer container 22 thus maintaining the performance of the product and dispensing acceptable during its usable life.

The conditioner composition 42 may include a propellant, which can also be referred to as a foaming or blooming agent. If a blooming agent is used with the composition 42, the pressure in the outer container 22 can be greater than the vapor pressure of the blooming agent, so that conditioner composition 42 may be dispensed from within the bag.

After the collapsible bag has been filled with the composition, the outer container may be pressurized from about 40 to about 160 psig, from about 50 to about 140 psig, from about 60 to about 90 psig (all measured at RT). In any case, the equilibrium pressure measured at a certain temperature cannot exceed the maximum allowable pressure of the container per the applicable local transport and safety regulations.

The product delivery device may alternatively or additionally comprise a dip tube 34 as shown in FIG. 6B. The dip tube 34 extends from a proximal end sealed to the valve assembly 28. The dip tube 34 may terminate at a distal end juxtaposed with the bottom of the outer container 22. The conditioner composition 42 and propellant 40 can intermix. The propellant 40 also accomplish the function of blooming agent. Both are co-dispensed in response to selective actuation of the valve assembly 28 by a user.

The product delivery device may be an aerosol pump dispenser and may not contain a dip tube or a collapsible bag, for instance, an inverted aerosol container.

The pressure of the propellant 40 within the outer container 22 provides for dispensing of the conditioner composition 42/co-dispensing of conditioner composition 42/propellant 40 to ambient, and optionally to a target surface. The target surface may include a surface to be cleaned or treated by the conditioner composition 42, hair, scalp, etc. Such dispensing occurs in response to the user actuating the valve assembly 28.

The outer container may be pressurized from about 20 to about 110 psig, more preferably from about 30 to about 90 psig, still more preferably from about 40 to about 70 psig (all measured after filling to the intended level at RT). In any case, the equilibrium pressure measured at a certain temperature cannot exceed the maximum allowable pressure of the container per the applicable local transport and safety regulations.

Referring to FIGS. 6A and 6B, the aerosol dispensers 20, and components thereof, may have a longitudinal axis, and may be axi-symmetric and can have a round cross section. Alternatively, the outer container 22, may be eccentric and may have a square, elliptical or other cross section. The outer container 22 and aerosol dispenser 20 may be nonrefillable and may be permanently sealed to prevent reuse without destruction and/or gross deformation of the aerosol dispenser 20. If desired, the outer container 22, collapsible bag 32, and/or dip tube 34, may be transparent or substantially transparent. If the outer container 22 and collapsible bag 32 (if present) are transparent, this arrangement can provide the benefit that the consumer knows when conditioner composition 42 is nearing depletion and allows improved communication of conditioner composition 42 attributes, such as color, viscosity, stability, etc. Alternatively or additionally, the outer container 22 and/or collapsible bag 32, etc. may be transparent and colored with like or different colors.

Non-limiting examples of suitable dispensers including a bag-on-valve and a dip-tube foamer can be found in U.S. Pat. No. 9,701,430, incorporated by reference.

Mechanical Pump Foamer

The conditioner composition can be stored and dispensed from a mechanical pump foam dispenser that may comprise a reservoir for holding the conditioner composition and a foam engine. The reservoir may be made from any suitable material selected from the group consisting of plastic, metal, alloy, laminate, and combinations thereof. The reservoir may be for one-time use. The reservoir may be removable from the mechanical pump foam dispenser. Alternatively, the reservoir may be integrated with the mechanical pump foam dispenser. There may be two or more reservoirs.

The conditioner composition can be stored and dispensed from a squeeze foam dispenser. An example of squeeze foamer is EZ'R available from Albéa.

Non-limiting examples of suitable pump dispensers include those described in WO 2004/078903, WO 2004/078901, and WO 2005/078063 and may be supplied by Albea (60 Electric Ave., Thomaston, Conn. 06787 USA) or Rieke Packaging Systems (500 West Seventh St., Auburn, Ind. 46706).

Foam Characteristics

A high-quality foam can be dispensed by the aerosol or mechanical pump foamer. A high-quality foam can appear creamy and conditioning. The foam can have many barely visible bubbles and no large bubbles. The foam can holds its shape and is not generally a runny mess after it is dispensed. The foam can be compliant but can still be easily uniformly spread across the user's hair.

The foam density can be from about 0.01 g/mL to about to about 0.4 g/mL, alternatively from about 0.03 to about 0.3 g/mL, alternatively from about 0.05 g/mL to about 0.25 g/mL, and alternatively from about 0.07 g/mL to about 0.2 g/mL. The foam density can be from about 0.1 g/mL to about 0.4 g/mL, alternatively 0.12 g/mL to about 0.35 g/mL, and alternatively 0.12g/mL to about 0.25 g/mL. The foam density can be measured by the Foam Density Method, described hereafter.

The compression force can be greater than 6 g, alternatively greater than 10 g, alternatively greater than 14 g. The compression force can be from about 10 g to about 40 g, alternatively from about 13 g to about 36 g, and alternatively from about 14 g to about 33 g. The compression force can be determined by the Foam Compression Test Method, described hereafter.

The dosage of foam can also have a bubble size distribution comprising an $R_{32}$ of from about 5 µm to about 100 µm, alternatively from about 5 µm to about 90 µm, alternatively from about 10 µm to about 60 µm, alternatively from about 20 µm to about 50 µm, and alternatively from about 25 µm to about 40 µm. the bubble size can be measured by the Kruss Lather Analyzer (Bubble Size) Method, described hereafter.

The dosage of foam can have a yield point of from about 5 Pa to about 100 Pa, alternatively about 10 Pa to about 100 Pa, alternatively from about 20 Pa to about 100 Pa, alternatively from about 25 Pa to about 100 Pa, and alternatively from about 38 Pa to about 100 Pa. The yield point can be measured by the Foam Rheology Method (Yield Point), described hereafter.

Additional description of consumer acceptable foams can be found in U.S. Pub. No. 2018/0110688, incorporated by reference.

Method of Treating Hair

The conditioner composition can be dispensed into a user's hand as a foam from an aerosol or mechanical pump foam dispenser. The dosage of foam can be easily spread across all or a portion of the user's hair. The conditioner can be a leave-on treatment or it can be rinsed. The conditioner composition can be used in before, after, or concurrently with a shampoo composition.

The conditioner composition can be used to treat hair by providing consumer acceptable conditioning and wet feel. The conditioner composition can have good silicone deposition and low fatty alcohol deposition and, in some instances, the conditioner composition can lead to improved deposition of silicone and/or less deposition of fatty alcohol as compared to traditional conditioner products.

The method of treating the hair described herein comprises (1) providing a conditioner composition, as described herein, in an aerosol foam dispenser, (2) dispensing the conditioner composition from the aerosol foam dispenser as a dosage of foam; (3) applying the foam to the hair; and (4) optionally rinsing the foam from the hair.

TEST METHODS

Cone/Plate Viscosity Measurement

The viscosities of the examples are measured by a Cone/Plate Controlled Stress Brookfield Rheometer R/S Plus, by Brookfield Engineering Laboratories, Stoughton, Mass. The cone used (Spindle C-75-1) has a diameter of 75 mm and 1° angle. The liquid viscosity is determined using a steady state flow experiment at constant shear rate of 2000 $s^{-1}$ and at temperature of 26.5° C. The sample size is 2.5 ml and the total measurement reading time is 3 minutes.

Differential Scanning Calorimetry

The melt transition behavior and temperature for the gel network may be obtained using differential scanning calorimetry (DSC) according to the following method. Utilizing a TA Instruments Q2000 DSC, approximately 15 mg of the gel network pre-mix or the final conditioner composition containing the gel network is placed into a Tzero aluminum hermetic DSC pan. The sample, along with an empty reference pan is placed into the instrument. The samples are analyzed using the following conditions/temperature program: Nitrogen Purge at a rate of 50.0 mL/min; Equilibrate @ 20.00° C.; Modulate+/–1.00° C./min every 60 seconds; until an isothermal is reach for 5.00 min; Ramp the temperature at a rate of 2.00° C./min to 90.00° C. The resulting DSC data is analyzed using TA Instruments Universal Analysis Software.

The use of DSC to measure the melt transition behavior and temperature for gel networks is further described by T. de Vringer et al., *Colloid and Polymer Science*, vol. 265, 448-457 (1987); and H. M. Ribeiro et al., *Intl. J. of Cosmetic Science*, vol. 26, 47-59 (2004).

Foam Compression

To measure the compressibility of the foam dispensed by the composition, a Texture Analyzer TA-XT Plus C (Stable Micro Systems Ltd, Surrey, UK) is used equipped with a 5 kg load cell and a disk probe having 1 inch diameter and 0.25 inches height at ambient conditions. The foam produced by the composition is dispensed into a cup (inner diameter 1.5 inches 1 inch deep) and the excess foam is removed so that the foam surface is smoothed with a spatula. The probe zero point is at the foam top surface. The probe is inserted into the foam sample using 2 gram-force. Data are collected for both force and distance. Compressive force (g) is measured at a compression rate of 2 mm/sec over a depth of 19 mm. The measurements are repeated at least three times and averaged. To determine the compressibility of the foam, the maximum observed force (g) is reported at the compression depth of 19 mm Foam Density Foam density is measured by placing a 100 mL beaker onto a mass balance, tarring the mass of the beaker and then dispensing product from the aerosol container into the 100 ml beaker until the volume of the foam is above the rim of the vessel. The foam is made level with the top of the beaker by scraping a spatula across it within 10 seconds of dispensing the foam above the rim of the vessel. The resulting mass of the 100 mL of foam is then divided by the volume (100) to determine the foam density in units of g/ml.

Foam Rheology Method (Yield Point)

Foam conditioner is applied to the AR1000 rheometer for foam oscillation stress sweep. 60 mm smooth acrylic plate is utilized for shear stress measurement. Measurement is made at 25C. The plate head is lowered to 1200 microns and excess foam is removed with a spatula so that drag does not occur during measurement. The measurement gap height is then lowered 1000 microns. Sweep occurs from 0.1 to 400 Pa. Data is analyzed via TA Rheology Advantage Data Analysis software. Yield point is determined at the point at which the oscillatory shear stress begins to deviate from its tangent. The yield point measurements are reported in Pa units.

Kruss Lather Analyzer (Bubble Size)

The commercially available Kruss lather analyzer DFA100, supplied from Kruss, is used to analyze the foam conditioner for the initial Sauter mean radius $R_{32}$ (bubble size). Conditioner foam is dispensed into the CY4571 column containing a prism. An internal stopper is placed into the column approximately 100 ml from the top of the chamber. The camera height is set to 244 mm and camera position is placed in the 3 slot. Structure foaming is captured at 2 frames per second for 120 seconds. Data analysis is performed on the Kruss Advance 1.5.1.0 software application version.

Shear Stress

Shear stress is measured by shear rate sweep condition with a rheometer available from TA Instruments with a mode name of ARG2. Geometry has 40 mm diameter, 2° C. cone angle, and gap of 49 μm. Shear rate is logarithmically increased from 0 to 1200/s for 1 min, and temperature is kept at 26.7° C. Share stress at a high shear rate of 950/s is measured and defined above.

EXAMPLES

The Examples and Comparative Examples, except Comparative Example A, herein can be made as follows:

1) The gel network base composition was made by adding the cationic surfactants and the high melting point fatty compounds to water with agitation, and heating to about 80° C. Then, the mixture is cooled down to room temperature. Unless otherwise specified, the gel network is cooled with a water bath with a cooling temperature from about 15 to about 25° C. lower than the composition until it reaches ambient temperature (20-25° C.).

2) All additional ingredients including electrolytes, polymers, silicone emulsions, preservatives and fragrances and additional water, if necessary, were added to the cooled product using a conventional mixing method.

It will be appreciated that other modifications of the conditioner compositions, and/or conditioner compositions within the skill of those in the formulation art can be undertaken without departing from the spirit and scope of this invention. All parts, percentages, and ratios herein are by weight unless otherwise specified. Some components may come from suppliers as dilute solutions. The amount stated reflects the weight percent of the active material, unless otherwise specified.

Comparative Ex A is prepared using the following process: The cationic surfactant (behentrimonium methosulfate), the fatty alcohols (cetyl aalcohol, stearyl alcohol), the disodium EDTS and the benzyl alcohol are mixed and heated to from about 66° C. to about 85° C. to form an oil phase. Separately, the other components of the gel matrix (preservative methylchloroisothiazoline/methylisothiazoline, and water) are mixed and heated to from about 20° C. to about 48° C. to form an aqueous phase. In Becomix® direct injection rotor-stator homogenizer, the oil phase is injected, and it takes 0.2 second or less for the oils phase to reach to a high shear field having an energy density of from $1.0 \times 10^5$ 7/m3 to $1.0 \times 10^7$ 7/m3 where the aqueous phase is already present. A gel network is formed. Then the composition is cooled down to room temperature The following are non-limiting examples of the conditioner compositions described herein.

TABLE 1

Figure 2:
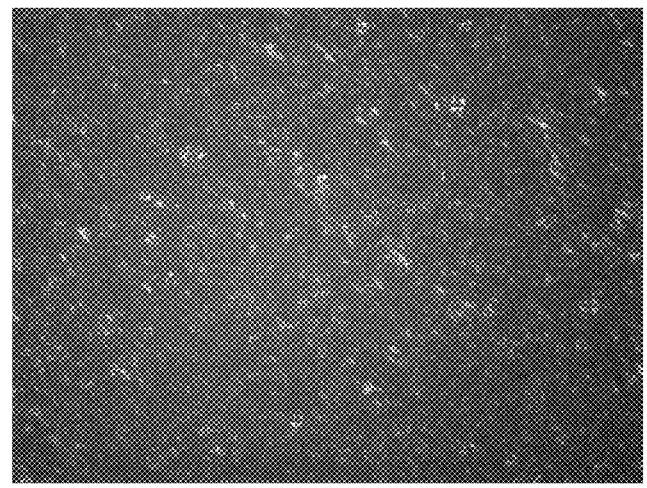
FIG. 2 is a photo taken under microscopy of the gel network structure of Example 2.
Figure 3:
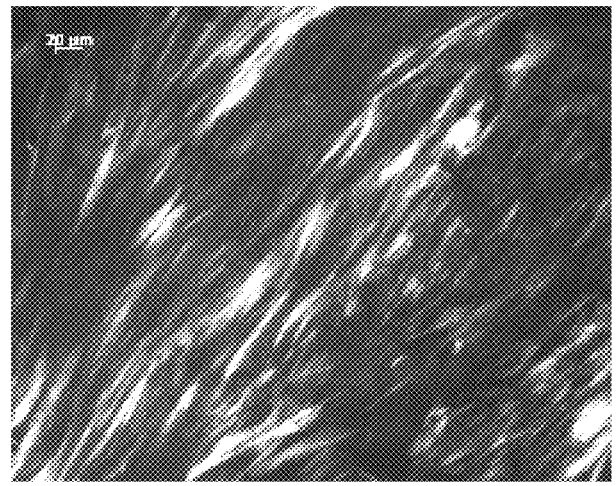
FIG. 3 is a photo taken under microscopy of the gel network structure of Comparative Example A.

|  | Ex. 1 | Ex. 2 | Comp. Ex. A | Comp. Ex. B |
|---|---|---|---|---|
| Behentrimonium Chloride (Cationic Surfactant) wt % (active)[1] | 4.3 | 5.00 |  | 4.83 |
| Behentrimonium Methosulfate (Cationic Surfactant) wt % (active)[2] |  |  | 4.3 |  |
| Cetyl Alcohol (C16 Fatty Alcohol) wt % (active)[3] | 0.84 | 1.18 | 0.84 | 0.66 |
| Stearyl Alcohol (C18 Fatty Alcohol) wt % (active) | 2.12 | 3.19 | 2.12 | 1.94 |
| Disodium EDTA wt % (active) | 0.10 | 0.10 | 0.10 | 0.10 |
| Benzyl Alcohol wt % (active) | 0.40 | 0.40 | 0.40 | 0.40 |
| Methylchloroisothiazoline/Methylisothiazolinone wt % (active)[4] | 0.0005 | 0.0005 | 0.0005 | 0.0005 |
| Water | Q.S. | Q.S. | Q.S. | Q.S. |
| Total Gel Network mole content (mol/100 g)* | 0.22 | 0.29 | 0.20 | 0.22 |
| Mole ratio of Cationic Surfactant to Fatty Alcohol | 1:1.04 | 1:1.33 | 1:1.22 | 1:0.80 |
| Mole ratio of cationic surfactant to Total Gel Network | 49 | 43 | 45 | 55 |
| Mole ratio of Total Fatty Alcohol to Total Gel Network | 51 | 57 | 55 | 45 |
| Mole ratio of C18 Fatty Alcohol to Total Fatty Alcohol | 70.72 | 70.72 | 70.72 | 70.72 |
| Mole ratio of C16 Fatty Alcohol to Total Fatty Alcohol | 29.28 | 29.28 | 29.28 | 29.28 |
| Cooling temperature of gel network base composition (ΔT in ° C.) | 25 | 25 | n/a | 25 |
| Shear stress of gel network base composition (Pa) @950 1/s | 188 | 112 | 258 | 265 |
| Rating of gel network structures | 4 | 5 | 1 | 2 |
| Image of gel network base composition | FIG. 1 | FIG. 2 | FIG. 3 | FIG. 4 |

Table 1 compares Examples 1 and 2 with Comparative Example A. Examples 1 and 2 have behentrimonium chloride and Comparative Example A has behentrimonium methosulfate. The gel network base compositions in Table 1 were examined under a light microscope (Zeiss Axioskop) at 40× with polarized light, see FIGS. 1-4, to determine the structure of the gel network.

The gel network was examined under a light microscope as follows: A droplet of the gel network composition is transferred onto a microscope slide using a pipette. The slide is covered with a coverslip. The microscope slide is placed in an optical microscope (Zeiss Axioskop) and observed using a magnification of 40× with polarized light. Observation of the microscope provides the relative populations of lamellar sheets and vesicles in five different measures:

1=almost all lamellar sheets (greater than ~75% lamella sheets)
2=mostly lamellar sheets (~60%-75% lamellar sheets)
3=approximately equal vesicles and sheets (~40-60% vesicles/sheets)
4=mostly vesicles (~60-75% vesicles)
5=almost all vesicles (greater than ~75% vesicles)

Examples 1 and 2 have a rating of 4 and 5, respectively. Therefore, all or most of the gel network in Examples 1 and 2 are vesicles. However, Comparative Examples A and B have lower ratings, 1 and 2, respectively. Therefore, all or most of the gel network in Examples A and B has a lamellar sheet structure.

Examples 1 and 2 have a lower shear stress, 188 Pa and 112 Pa, respectively, as compared to Comparative Examples A and B. Without being bound by theory, it is believed that the chloride ion in the cationic surfactant contributes to forming all vesicles or mostly vesicles in the gel network. Since the shear stress of the gel network base composition is lower, it is likely that Examples 1 and 2 will dispense as a high-quality foam from an aerosol or mechanical pump foamer. Therefore, Examples 1 and 2 may be preferred by consumers.

Figure 7:
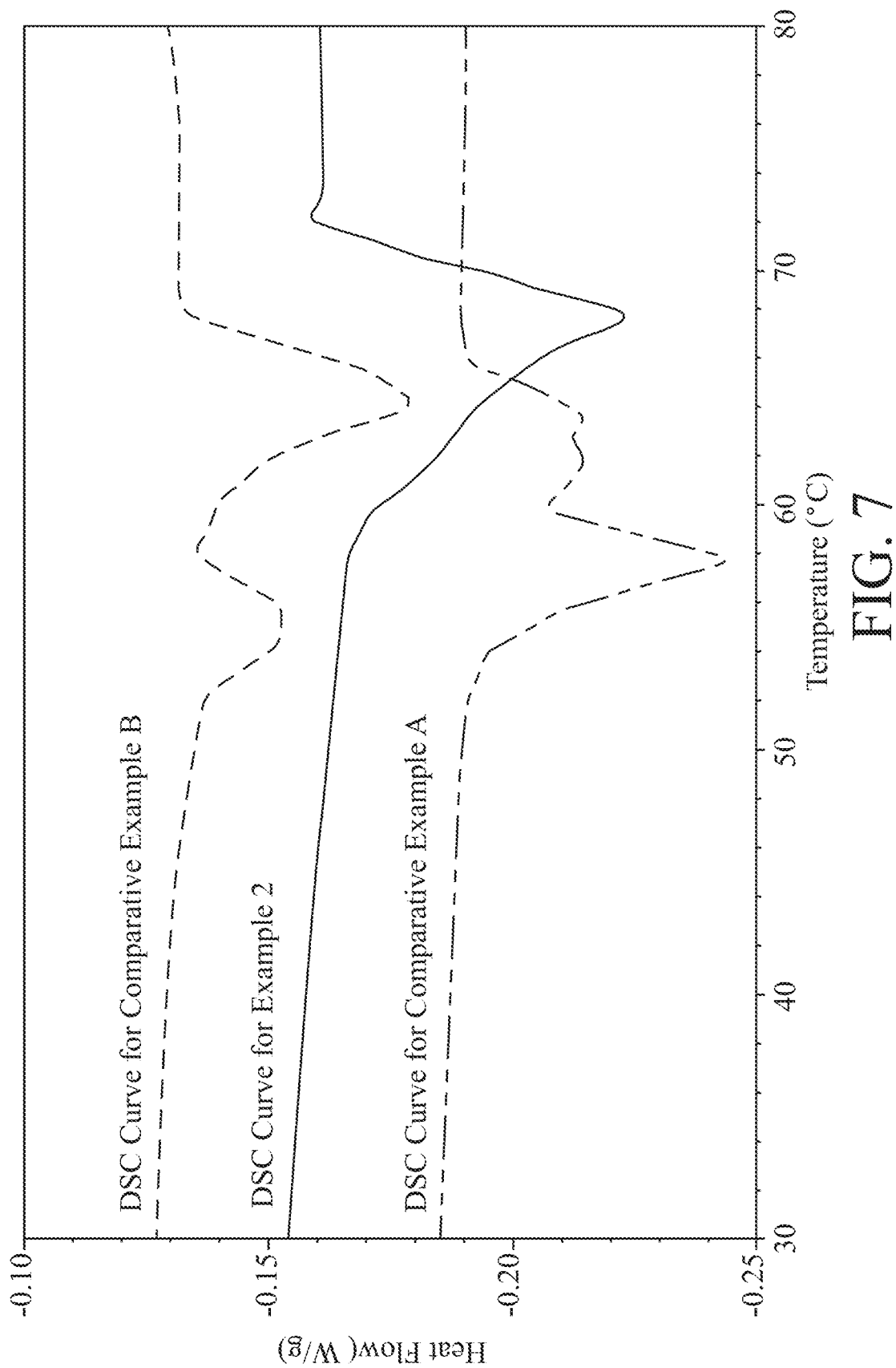
FIG. 7 shows the melt transition behavior of the gel network, as measured by the Differential Scanning calorimetry (DSC) Test Method, of Example 2 and Comparative Examples A and B.

FIG. 7 shows the melt transition behavior of the gel network of Example 2 and Comparative Examples A and B. The curves were made according to the Differential Scanning Calorimetry Test Method, described herein. The DSC curve for Example 2 shows only one peak and this indicates that this Example has a uniform gel network phase. However, Comparative Examples A and B have more than one peak, which indicates that the gel network is non-uniform.

TABLE 2

Gel Network Compositions

|  | Ex.3 | Ex.2 | Ex.4 | Ex.5 | Ex.6 |
| --- | --- | --- | --- | --- | --- |
| Behentrimonium Chloride (Cationic Surfactant) wt % (active)[1] | 3.51 | 5.00 | 4.53 | 3.78 | 5.00 |
| Cetyl Alcohol (C16 Fatty alcohol) wt % (active) [2] | 0.87 | 1.18 | 1.06 | 0.89 | 1.08 |
| Stearyl Alcohol (C18 Fatty Alcohol) wt % (active) [3] | 2.58 | 3.19 | 2.87 | 2.39 | 2.92 |
| Disodium EDTA wt % (active) | 0.10 | 0.10 | 0.10 | 0.10 | 0.10 |
| Benzyl Alcohol wt % (active) | 0.40 | 0.40 | 0.40 | 0.40 | 0.40 |
| Methylchloroisothiazoline/ Methylisothiazolinone wt % (active) [4] | 0.0005 | 0.0005 | 0.0005 | 0.0005 | 0.0005 |
| Water | Q.S. | Q.S. | Q.S. | Q.S. | Q.S. |
| Total Gel Network Mole Content (mol/100 g)* | 0.22 | 0.29 | 0.26 | 0.26 | 0.28 |
| Mole Ratio of Cationic Surfactant to Fatty Alcohol | 1:1.5 | 1:1.3 | 1:1.3 | 1:1.3 | 1:1.2 |
| Mole Ratio of Cationic Surfactant to Total Gel Network | 40 | 43 | 43 | 43 | 45 |
| Mole Ratio of Total Fatty Alcohol to Total Gel Network | 60 | 57 | 57 | 57 | 55 |
| Mole Ratio of C18 Fatty Alcohol to Total Fatty Alcohol | 70.72 | 70.72 | 70.72 | 70.72 | 70.72 |
| Mole Ratio of C16 Fatty Alcohol to Total Fatty Alcohol | 29.28 | 29.28 | 29.28 | 29.28 | 29.28 |
| Cooling temperature of gel network base composition (ΔT in ° C.) | 25 | 25 | 25 | 25 | 25 |
| Shear stress of gel network base composition (Pa) @950 1/s | 188 | 112 | 92 | 69 | 122 |

TABLE 3

Gel Network Compositions

|  | Ex.7 | Ex.8 | Ex.9 | Ex.10 | Ex.11 |
| --- | --- | --- | --- | --- | --- |
| Behentrimonium Chloride (Cationic Surfactant) wt % (active)[1] | 4.74 | 3.95 | 4.95 | 4.13 | 4.39 |
| Cetyl Alcohol (C16 Fatty alcohol) wt % (active) [2] | 1.03 | 0.8 | 0.99 | 0.83 | 0.78 |
| Stearyl Alcohol (C18 Fatty Alcohol) wt % (active) [3] | 2.77 | 2.37 | 2.67 | 2.22 | 2.1 |

TABLE 3-continued

Gel Network Compositions

| | Ex.7 | Ex.8 | Ex.9 | Ex.10 | Ex.11 |
|---|---|---|---|---|---|
| Disodium EDTA wt % (active) | 0.10 | 0.10 | 0.10 | 0.10 | 0.10 |
| Benzyl Alcohol wt % (active) | 0.40 | 0.40 | 0.40 | 0.40 | 0.40 |
| Methylchloroisothiazoline/ Methylisothiazolinone wt % (active) [4] | 0.0005 | 0.0005 | 0.0005 | 0.0005 | 0.0005 |
| Water | Q.S. | Q.S. | Q.S. | Q.S. | Q.S. |
| Total Gel Network Mole Content (mol/100 g)* | 0.26 | 0.22 | 0.26 | 0.22 | 0.22 |
| Mole Ratio of Cationic Surfactant to Fatty Alcohol | 1:1.2 | 1:1.2 | 1:1.1 | 1:1.1 | 1:1 |
| Mole Ratio of Cationic Surfactant to Gel Network | 45 | 45 | 47 | 47 | 50 |
| Mole Ratio of Total Fatty Alcohol to Gel Network | 55 | 55 | 53 | 53 | 50 |
| Mole Ratio of C18 Fatty Alcohol to Total Fatty Alcohol | 70.72 | 70.72 | 70.72 | 70.72 | 70.72 |
| Mole Ratio of C16 Fatty Alcohol to Total Fatty Alcohol | 29.28 | 29.28 | 29.28 | 29.28 | 29.28 |
| Cooling temperature of gel network base composition ($\Delta T$ in ° C.) | 25 | 25 | 25 | 25 | 25 |
| Shear stress of gel network base composition (Pa) @950 1/s | 113 | 92 | 152 | 134 | 189 |

TABLE 4

Gel Network Compositions

| | Comp. Ex. C | Comp. Ex. D | Comp. Ex. B | Comp. Ex. E | Comp. Ex. F |
|---|---|---|---|---|---|
| Behentrimonium Chloride (Cationic Surfactant) wt % (active)[1] | 4.92 | 4.92 | 4.83 | 4.92 | 4.95 |
| Cetyl Alcohol (C16 Fatty alcohol) wt % (active) [2] | 2.03 | 1.62 | 0.66 | 0.58 | 0.47 |
| Stearyl Alcohol (C18 Fatty Alcohol) wt % (active) [3] | 5.48 | 4.36 | 1.94 | 1.57 | 1.27 |
| Disodium EDTA wt % (active) | 0.10 | 0.10 | 0.10 | 0.10 | 0.10 |
| Benzyl Alcohol wt % (active) | 0.40 | 0.40 | 0.40 | 0.40 | 0.40 |
| Methylchloroisothiazoline/ Methylisothiazolinone wt % (active) [4] | 0.0005 | 0.0005 | 0.0005 | 0.0005 | 0.0005 |
| Water | Q.S. | Q.S. | Q.S. | Q.S. | Q.S. |
| Total Gel Network Mole Content (mol/100 g)* | 0.41 | 0.35 | 0.22 | 0.20 | 0.19 |
| Mole Ratio of Cationic Surfactant to Fatty Alcohol | 1:2.3 | 1:1.9 | 1:0.8 | 1:0.7 | 1:0.5 |
| Mole Ratio of Cationic Surfactant to Total Gel Network | 30 | 35 | 55 | 60 | 65 |
| Mole Ratio of Total Fatty Alcohol to Total Gel Network | 70 | 65 | 45 | 40 | 35 |
| Mole Ratio of C18 Fatty Alcohol to Total Fatty Alcohol | 70.72 | 70.72 | 70.72 | 70.72 | 70.72 |
| Mole Ratio of C16 Fatty Alcohol to Total Fatty Alcohol | 29.28 | 29.28 | 29.28 | 29.28 | 29.28 |
| Cooling temperature of gel network base composition ($\Delta T$ in ° C.) | 25 | 25 | 25 | 25 | 25 |
| Shear stress of gel network base composition (Pa) @950 1/s | 701 | 424 | 265 | 358 | 433 |

Table 2, Table 3, and Table 4 include examples of conditioner compositions. Examples 2-11 in Table 2 and Table 3 are examples with a shear stress from 69 Pa to 189 Pa. The low shear indicates that these examples have gel network vesicles, as opposed to laminar sheets. The shear stress of the gel network composition in these examples will likely produce a high-quality foam that may be consumer preferred.

Table 4 includes comparative examples B-F. These examples have a shear that is too high, from 265 Pa to 701 Pa, to produce a consumer acceptable foam. As discussed above (Table 1 and FIG. 2), Example B, E, and F have a gel network that is composed of a lamella structure with a higher than 50% sheet shape of lamella structure, which causes the high shear stress. Examples C and D have higher shear stress is likely because of higher level of fatty alcohol in the composition which causing higher viscosity. Thus, the mole ratio of cationic surfactant to fatty alcohol can also influence the viscosity of the composition.

The differences in shear stress and lamella structure in Examples 3-11 and Comparative Examples B-F, may largely be caused by varying the mole ratio of the cationic surfactant to the fatty alcohol. In Examples 3-11, the ratio ranges from 1:1.5 to 1:1. Comparative Example C and D have a ratio from 1:2.3 to 1:1.9, which is lower than the ratio in Examples 3-11. Comparative Examples B, E, and F have a ratio from 1:0.8 to 1:0.5, which is higher than the ratio in Examples 3-11.

TABLE 5

| Gel Network Composition | | | |
|---|---|---|---|
| | Ex.12 | Ex.13 | Comp. Ex. G |
| Behentrimonium Chloride (Cationic Surfactant) wt % (active)[1] | 5.00 | 5.00 | 5.00 |
| Cetyl Alcohol (C16 Fatty alcohol) wt % (active) [2] | 1.18 | 1.18 | 1.18 |
| Stearyl Alcohol (C18 Fatty Alcohol) wt % (active) [3] | 3.19 | 3.19 | 3.19 |
| Disodium EDTA wt % (active) | 0.10 | 0.10 | 0.10 |
| Benzyl Alcohol wt % (active) | 0.40 | 0.40 | 0.40 |
| Methylchloroisothiazoline/ Methylisothiazolinone wt % (active) [4] | 0.0005 | 0.0005 | 0.0005 |
| Water | Q.S. | Q.S. | Q.S. |
| Total Gel Network Mole Content (mol/100 g)* | 0.29 | 0.29 | 0.29 |
| Mole Ratio of Cationic Surfactant to Fatty Alcohol | 1:1.3 | 1:1.3 | 1:1.3 |
| Mole Ratio of Cationic Surfactant to Total Gel Network | 43 | 43 | 43 |
| Mole Ratio of Total Fatty Alcohol to Total Gel Network | 57 | 57 | 57 |
| Mole Ratio of C18 Fatty Alcohol to Total Fatty Alcohol | 70.72 | 70.72 | 70.72 |
| Mole Ratio of C16 Fatty Alcohol to Total Fatty Alcohol | 29.28 | 29.28 | 29.28 |
| Cooling temperature of gel network base composition ($\Delta T$ in ° C.) | 25 | 15 | 10 |
| Shear stress of gel network base composition (Pa) @950 1/s | 112 | 78 | 46 |

Table 5 compares Examples 12 and 13 with Comparative Example G. All three compositions have the same ingredients. However, the data in Table 5 shows that the cooling rate can impact the shear stress/viscosity of the gel networks. Comparative Example G was cooled at a slower rate, as compared to Examples 12 and 13 and Comparative Example G has a shear stress of 46 Pa, which is too low to produce a high quality, consumer acceptable foam see Table 8, below.

TABLE 6

| Conditioner Compositions | | | | | | |
|---|---|---|---|---|---|---|
| | Ex. 14 | Ex. 15 | Ex. 16 | Ex. 17 | Ex. 18 | Ex. 19 |
| Behentrimonium Chloride (Cationic Surfactant) wt % (active)[1] | 3.51 | 5.00 | 5.00 | 5.00 | 5.00 | 4.53 |
| Cetyl Alcohol (C16 Fatty alcohol) wt % (active) [2] | 0.87 | 1.18 | 1.18 | 1.18 | 1.18 | 1.06 |
| Stearyl Alcohol (C18 Fatty Alcohol) wt % (active) [3] | 2.58 | 3.19 | 3.19 | 3.19 | 3.19 | 2.87 |
| Disodium EDTA wt % (active) | 0.10 | 0.10 | 0.10 | 0.10 | 0.10 | 0.10 |
| Benzyl Alcohol wt % (active) | 0.40 | 0.40 | 0.40 | 0.40 | 0.40 | 0.40 |
| Methylchloroisothiazoline/ Methylisothiazolinone wt % (active) [4] | 0.0005 | 0.0005 | 0.0005 | 0.0005 | 0.0005 | 0.0005 |
| Water | Q.S. | Q.S. | Q.S. | Q.S. | Q.S. | Q.S. |
| AH0255 Si emulsion[11] | 4 | | | | | |
| Aminopropyl Terminated Polydimethylsiloxane[12] | | | | 4 | 4 | |
| Silicone Quaternium-26[13] | | | 4 | | | |
| Soybean Oil[14] | | 4 | | | | 4 |
| Perfume | 2.0 | 2.0 | 2.0 | 2.0 | 2.0 | 2.0 |
| Total Gel Network Mole Content (mol/100 g)* | 0.22 | 0.29 | 0.29 | 0.29 | 0.29 | 0.26 |
| Mole Ratio of Cationic Surfactant to Fatty Alcohol | 1:1.5 | 1:1.3 | 1:1.3 | 1:1.3 | 1:1.3 | 1:1.3 |
| Mole Ratio of Cationic Surfactant to Total Gel Network | 40 | 43 | 43 | 43 | 43 | 43 |
| Mole Ratio of Total Fatty Alcohol to Total Gel Network | 60 | 57 | 57 | 57 | 57 | 57 |
| Mole Ratio of C18 Fatty Alcohol to Total Fatty Alcohol | 70.72 | 70.72 | 70.72 | 70.72 | 70.72 | 70.72 |
| Mole Ratio of C16 Fatty Alcohol to Total Fatty Alcohol | 29.28 | 29.28 | 29.28 | 29.28 | 29.28 | 29.28 |
| Shear stress of gel network base composition (Pa) @950 1/s | 188 | 112 | 112 | 112 | 112 | 92 |
| Viscosity (cP) | 44 | 910 | 33 | 717 | 717 | 24 |

TABLE 7

Conditioner Compositions with Propellant

| | Ex. 14' | Ex. 15' | Ex. 16' | Ex. 17' | Ex. 18' | Ex. 19' |
|---|---|---|---|---|---|---|
| | Conditioner Composition from Table 6 (wt. %) | | | | | |
| | 96 | 93.5 | 94.5 | 96 | 96 | 96 |
| | Ex. 14 | Ex. 15 | Ex. 16 | Ex. 17 | Ex. 18 | Ex. 19 |
| A46[5] (wt. %) | 4.0 | | | | 4.0 | 4.0 |
| A70[6] (wt. %) | | | | 4.0 | | |
| HFO[7] (wt. %) | | 6.5 | 5.5 | | | |
| Foam Density (g/ml) | 0.07 | 0.12 | 0.13 | 0.08 | 0.09 | 0.10 |
| Foam Compression Force (g) | 21 | 22 | 16 | 26 | 22 | 20 |

TABLE 8

Conditioner Compositions

| | Ex. 20 | Ex. 21 | Ex. 22 | Ex. 23 | Ex. 24 | Comp. Ex. G |
|---|---|---|---|---|---|---|
| Behentrimonium Chloride (Cationic Surfactant) wt % (active)[1] | 3.95 | 3.95 | 4.13 | 4.39 | 5.00 | 5.00 |
| Cetyl Alcohol (C16 Fatty alcohol) wt % (active)[2] | 0.8 | 0.8 | 0.83 | 0.78 | 1.18 | 1.18 |
| Stearyl Alcohol (C18 Fatty Alcohol) wt % (active)[3] | 2.37 | 2.37 | 2.22 | 2.1 | 3.19 | 3.19 |
| Disodium EDTA wt % (active) | 0.10 | 0.10 | 0.10 | 0.10 | 0.10 | 0.10 |
| Benzyl Alcohol wt % (active) | 0.40 | 0.40 | 0.40 | 0.40 | 0.40 | 0.40 |
| Methylchloroisothiazoline/ Methylisothiazolinone wt % (active)[4] | 0.0005 | 0.0005 | 0.0005 | 0.0005 | 0.0005 | 0.0005 |
| Total Gel Network Mole Content (mol/100 g)* | 0.22 | 0.22 | 0.22 | 0.22 | 0.29 | 0.29 |
| Mole Ratio of Cationic Surfactant to Fatty Alcohol | 1:1.2 | 1:1.2 | 1:1.1 | 1:1 | 1:1.3 | 1:1.3 |
| Mole Ratio of Cationic Surfactant to Total Gel Network | 45 | 45 | 47 | 50 | 43 | 43 |
| Mole ratio of Total Fatty Alcohol to Total Gel Network | 55 | 55 | 53 | 50 | 57 | 57 |
| Mole Ratio of C18 Fatty Alcohol to Total Fatty Alcohol | 70.72 | 70.72 | 70.72 | 70.72 | 70.72 | 70.72 |
| Mole Ratio of C16 Fatty Alcohol to Total Fatty Alcohol | 29.28 | 29.28 | 29.28 | 29.28 | 29.28 | 29.28 |
| Shear stress of gel network base composition (Pa) @950 1/s | 92 | 92 | 134 | 189 | 112 | 46 |
| Aminopropyl Terminated Polydimethylsiloxane[12] | 4 | | 4 | | 4 | 4 |
| Soybean Oil[14] | | 4 | | 4 | | |
| Perfume | 2.0 | 2.0 | 2.0 | 2.0 | 2.0 | 2.0 |
| Water | Q.S. | Q.S. | Q.S. | Q.S. | Q.S. | Q.S. |
| Viscosity (cP) | 1041 | 1809 | 1232 | 3412 | 910 | 15 |

TABLE 9

Conditioner Compositions with Propellant

|  | Ex. 20' | Ex. 21' | Ex. 22' | Ex. 23' | Ex. 24' | Comp. Ex. G' |
|---|---|---|---|---|---|---|
|  | \multicolumn{6}{c}{Conditioner Composition from Table 8 (wt. %)} | | | | | |
|  | 93.5 Ex. 20 | 93.5 Ex. 21 | 94.5 Ex. 22 | 96 Ex. 23 | 92.5 Ex. 20 | 94 Comp. Ex. G |
| A46[5] (wt. %) |  |  |  | 4.0 |  |  |
| HFO[7] (wt. %) | 6.5 | 6.5 | 5.5 |  | 7.5 | 6 |
| Foam Density (g/ml) | 0.11 | 0.12 | 0.20 | 0.10 | 0.10 | 0.15 |
| Foam Compression Force (g) | 17 | 25 | 21 | 24 | 15 | 6 |

Table 6 and Table 8 includes Example 13-23 and Comparative Example G and Table 8 and Table 9 includes these examples with a propellant. These compositions were dispensed from a dip tube aerosol foamer. Examples 14-24 had a shear stress from 92 Pa to 189 Pa and a cationic surfactant to gel network mole ratio from 92 to 189. The foam produced from the aerosol dip tube foamer had a foam density from 0.07 g/mL to 0.2 g/mL and a foam compression force of 15-26 g. The foam from these examples is a consumer acceptable, high-quality foam. The foam is creamy and compliant.

Comparative Example G has a shear stress that is too low. The foam from this composition is not consumer acceptable it has an unattractive, sloppy, not creamy appearance that is easily collapsed.

TABLE 10

Conditioner Compositions

|  | Ex. 25 | Ex. 26 | Ex. 27 | Ex. 28 | Ex. 29 | Ex. 30 |
|---|---|---|---|---|---|---|
| Behentrimonium Chloride (Cationic Surfactant) wt % (active)[1] | 5.00 | 5.00 | 5.00 | 5.00 | 4.53 | 4.53 |
| Cetyl Alcohol (C16 Fatty alcohol) wt % (active)[2] | 1.18 | 1.18 | 1.18 | 1.18 | 1.06 | 1.06 |
| Stearyl Alcohol (C18 Fatty Alcohol) wt % (active)[3] | 3.19 | 3.19 | 3.19 | 3.19 | 2.87 | 2.87 |
| Disodium EDTA wt % (active) | 0.10 | 0.10 | 0.10 | 0.10 | 0.10 | 0.10 |
| Benzyl Alcohol wt % (active) | 0.40 | 0.40 | 0.40 | 0.40 | 0.40 | 0.40 |
| Methylchloroisothiazoline/ Methylisothiazolinone wt % (active)[4] | 0.0005 | 0.0005 | 0.0005 | 0.0005 | 0.0005 | 0.0005 |
| Total Gel Network Mole Content (mol/100 g)* | 0.29 | 0.29 | 0.29 | 0.29 | 0.26 | 0.26 |
| Mole Ratio of Cationic Surfactant to Fatty Alcohol | 1:1.3 | 1:1.3 | 1:1.3 | 1:1.3 | 1:1.3 | 1:1.3 |
| Mole Ratio of Cationic Surfactant to Total Gel Network | 43 | 43 | 43 | 43 | 43 | 43 |
| Mole Ratio of Total Fatty Alcohol to Total Gel Network | 57 | 57 | 57 | 57 | 57 | 57 |
| Mole Ratio of C18 Fatty Alcohol to Total Fatty Alcohol | 70.72 | 70.72 | 70.72 | 70.72 | 70.72 | 70.72 |
| Mole Ratio of C16 Fatty Alcohol to Total Fatty Alcohol | 29.28 | 29.28 | 29.28 | 29.28 | 29.28 | 29.28 |
| Shear stress of gel network base composition (Pa) @950 1/s | 112 | 112 | 112 | 112 | 92 | 92 |
| Aminopropyl Terminated Polydimethylsiloxane | 4 | 4 | 4 | 4 |  |  |
| Soybean Oil |  |  |  |  | 4 | 2 |
| Salt | 0.4 |  |  |  |  |  |
| Ultrage 300 (PQ37)[8] |  | 0.4 |  |  | 0.4 | 0.2 |
| Polysurf™ 67 CS[9] |  |  | 0.4 |  |  |  |
| Natrosol™ plus 330CS[10] |  |  |  | 0.4 |  |  |
| Perfume | 2.0 | 2.0 | 2.0 | 2.0 | 2.0 | 2.0 |
| Water | Q.S. | Q.S. | Q.S. | Q.S. | Q.S. | Q.S. |
| Viscosity (cP) | 5136 | 2253 | 8418 | 5042 | 1610 | 1051 |

TABLE 11

Conditioner Compositions with Propellant

|  | Ex. 25' | Ex. 26' | Ex. 27' | Ex. 28' | Ex. 29' | Ex. 30' |
|---|---|---|---|---|---|---|
|  | \multicolumn{6}{c}{Conditioner Composition from Table 10 (wt. %)} | | | | | |
|  | 94 Ex. 25 | 94 Ex. 26 | 94 Ex. 27 | 94 Ex. 28 | 94 Ex. 29 | 94 Ex. 30 |
| HFO[7] | 6.0 | 6.0 | 6.0 | 6.0 | 6.0 | 6.0 |
| Foam Density (g/ml) | 0.18 | 0.18 | 0.12 | 0.13 | 0.14 | 0.14 |
| Foam Compression Force (g) | 32 | 28 | 30 | 32 | 23 | 16 |

*The Total Gel Network mole content is calculated by adding the total moles of cationic surfactant with the total moles of fatty alcohol.
1. Behentrimonium Chloride/IPA (Genamin KDMP), available from Clariant™ at 80% active level
2. Cetyl alcohol, 95% active level available from Procter & Gamble®
3. Stearyl alcohol, 97% active level, available from Procter & Gamble®
4. Kathon CG available from Dow (1.5 wt % active)
5. Blowing Agent A46 (Isobutane and Propane) Diversified CPC International (Channahon, Ill., USA)
6. Blowing Agent A70 (Isobutane and Propane) Diversified CPC International (Channahon, Ill., USA)
7. Blowing Agent HFO (Trans 1,3,3,3 Tetrafluroprop-1-ene) from Honeywell®
8. Cosmedia® Ultragel 300-Cationic Acrylic homopolymer available from Ashland™ Chemicals
9. Polysurf™ 67CS-Hydrophobically Modified hydroxyethylcellulose available from Ashland™ Chemicals
10. Natrosol™ plus 330CS-Hydrophobically Modified hydroxyethylcellulose available from Ashland™ Chemicals
11. AH0255-amodimethicone, 20% active level, available from Wacker
12 Aminopropyl terminated polydimethylsiloxane, available from by Dow Corning®
13. Silicone Quaternium-26 supplied by Momentive®
14. Soybean Oil, available from Cargill®

Table 10 includes Example 25-30 and Table 11 includes these examples with a propellant. These compositions were dispensed from an aerosol dip tube foamer. Examples 25-30 had a shear stress from 92 Pa to 112 Pa and a cationic surfactant to gel network mole ratio of 43. The foam produced had a foam density from 0.12 g/mL to 0.18 g/mL and a foam compression force of 16 to 32 g. The foam from these examples is a consumer acceptable, high-quality foam. The foam is creamy and compliant.

Combinations

A. A hair conditioner composition comprising:
  a. a gel network composition comprising:
    from about 1 wt. % to about 10 wt. % of a cationic surfactant having a chloride counterion; and
    from about 1 wt. % to about 10 wt. % of a fatty alcohol selected from the group consisting of cetyl alcohol, stearyl alcohol, behenyl alcohol, and combinations thereof;
    wherein the gel network composition comprises all vesicles or mostly vesicles;
  b. from about 60 wt. % to about 90 wt. % water;
  c. from about 1 wt. % to about 10 wt. % propellant;
    wherein the mole ratio of cationic surfactant to fatty alcohol is from about 0.55 to about 1.2;
    wherein the composition comprises a liquid phase viscosity from about 5 cps to about 10,000 cP.
B. The hair conditioner composition according to Paragraph B wherein the conditioner composition comprises a liquid phase viscosity of from about 5 cP (5 mPa·s) to about 10,000 cP (10,000 mPa·s), preferably from about 10 cP (10 mPa·s) to about 8000 cP (8000 mPa·s), more preferably from about 20 cP (20 mPa·s) to about 5000 cP (5000 mPa·s), and even more preferably from about 75 cP (75 mPa·s) to about 2000 cP (2000 mPa·s), as measured by the Cone/Plate Viscosity Measurement, described herein.
C. The hair conditioner according to Paragraphs A-B, wherein the cationic surfactant having a chloride counter ion is selected from the group consisting of behenyltrimethyl- ammonium chloride, cetyl trimethyl ammonium chloride, stearyl trimethyl ammonium chloride, ditallow alkyl dimethyl ammonium chloride, dihydrogenated tallow alkyl dimethyl ammonium chloride, distearyl dimethyl ammonium chloride, dicetyl dimethyl ammonium chloride, and combinations thereof. The cationic surfactant can be behenyltrimethylammonium chloride, and combinations thereof.
D. The hair conditioner composition according to paragraph C, wherein the catonic surfactant comprises behentrimonium chloride.
E. The hair conditioner composition according to paragraphs A-D, wherein the composition comprises from about 2.5 wt. % to about 6 wt. % fatty alcohol.
F. The hair conditioner composition according to paragraphs A-E, wherein the mole ratio of cationic surfactant to fatty alcohol is from about 0.6 to about 1.15, preferably from about 0.63 to about 1.1, more preferably from about 0.65 to about 1.05, and even more preferably from about 0.66 to about 1.
G. The hair conditioner composition according to paragraphs A-F, wherein the gel network comprises more than 50% gel network vesicles, preferably more than 60% vesicles, more preferably more than 70% vesicles, and even more preferably more than 80% vesicles.
H. The hair conditioner composition according to paragraphs A to G, wherein the conditioner composition comprises from about 1.5 wt. % to about 8 wt. % cationic surfactant, preferably from about 1.8 wt. % to about 7 wt. %, more preferably from about 2 wt. % to about 6.5 wt. %, more preferably from about 2.5% to about 6%, and even more preferably from about 3 wt. % to about 5.5 wt. %.
I. The hair conditioner composition according to paragraphs A to H, wherein the gel network composition comprises a shear stress greater than 50 and less than 200 Pa, preferably from about 55 Pa to about 260 Pa, more preferably from about 60 Pa to about 200 Pa, and even more preferably from about 67 Pa to about 190 Pa, as determined by the Shear Stress Test Method, described herein.
J. The conditioner composition according to paragraphs A to I, wherein the gel network composition comprises from about 1.5 wt. % to about 9 wt. % fatty alcohol, preferably from about 2 wt. % to about 8.5 wt. % gel network, more preferably from about 2 wt. % to about 7 wt. %, and even more preferably from about 2.5 wt. % to about 5 wt. %.
K. The conditioner composition according to paragraphs A to I, wherein the composition further comprises from about 0.5% to about 8% of one or more oils, preferably from about 1% to about 6%, more preferably from about 1.5% to about 5%, and even more preferably from about 2% to about 4% of one or more oils, by weight of the conditioner composition.
L. The conditioner composition according to paragraph K, wherein the one or more oils comprise a particle size from about 1 nm to about 500 nm, preferably from about 5 nm to about 250 nm, more preferably from about 10 nm to about 100 nm, and even more preferably about 12 nm to about 50 nm.
M. The conditioner composition according to paragraphs K-L, wherein the one or more oils are substantially free of silicone and/or free of silicone.
N. The conditioner composition according to paragraphs K-L, wherein the one or more oils comprise silicone.
O. The conditioner composition according to paragraphs A-N, further comprising from about 0.75% to about 7% perfume, preferably from about 1.5% to about 5%, and more preferably from about 1.25% to about 4% perfume.

P. The conditioner composition according to paragraphs A-O, wherein the conditioner composition further comprises from about 60 wt. % to about 90 wt. % water, preferably from about 65% to about 87.5% water, more preferably from about 67.5% to about 85% water, and even more preferably from about 72.5% to about 80% water.

Q. The conditioner composition according to paragraphs A-P, comprising from about 2% to about 10% propellant, more preferably from about 3% to about 8% propellant, and even more preferably from about 4% to about 7% propellant, by weight of the conditioner.

R. The conditioner composition according to paragraphs A-Q, wherein the propellant comprises 1,3,3,3-tetrafluoropropene.

S. The conditioner composition according to paragraphs A-Q, wherein the propellant is selected from the group consisting of isobutane, propane, butane, and combinations thereof.

T. A method of treating hair comprising:
  a. providing the conditioner composition of paragraphs A-S in an aerosol foam dispenser;
  b. dispensing the conditioner composition from the foam dispenser as a dosage of foam;
  c. applying the foam to the hair;
  d. optionally rinsing the foam from the hair.

U. The method according to paragraph T, wherein the foam dispenser is an aerosol dip tube foam dispenser.

V. The method according to paragraph T-U, wherein the dosage of foam comprises a foam density from about 0.01 g/mL to about to about 0.4 g/mL, preferably from about 0.03 to about 0.3 g/mL, more preferably from about 0.05 g/mL to about 0.25 g/mL, and even more preferably from about 0.07 g/mL to about 0.2 g/mL.

W. The method according to paragraph T-V, wherein dosage of foam comprises a bubble size distribution comprising an $R_{32}$ of from about 5 µm to about 100 µm, preferably from about 5 µm to 90 µm, more preferably from about 10 µm to about 60 µm, and even more preferably from about 20 µm to about 50 µm, according to the Kruss Lather Analyzer (Bubble Size) Method, described herein.

X. The method according to paragraph T-W, wherein the dosage of foam comprises a yield point of from about 5 Pa to about 100 Pa, preferably from about 20 Pa to about 100 Pa, more preferably from about 25 Pa to about 100 Pa, and even more preferably from about 38 Pa to about 100 Pa. The yield point can be measured by the Foam Rheology Method (Yield Point), described herein.

Y. A method of making the conditioner composition of paragraphs A-S comprising:
  a. heating the cationic surfactant and the fatty alcohol to at least 70° C., preferably at least 80° C.;
  b. cooling the cationic surfactant and the fatty alcohol with a cooling bath with a temperature from about 15° C. to about 25° C. lower than the composition to form a gel network base composition;
  c. combining the gel network base composition with the water to form the conditioner composition.

Z. The method of paragraph Y, wherein the composition is cooled to ambient temperature wherein the cooling temperature at least 18° C. lower than the composition, preferably at least 20° C., more preferably at least 22° C., and even more preferably at least 25° C.

AA. The method of paragraph Y, wherein the composition is cooled to ambient temperature wherein the cooling temperature is from about 18° C. to about 25° C. lower than the composition, and alternatively from about 20° C. to about 25° C. lower than the composition.

BB. Use of the hair care composition according to Paragraphs A-S, for providing a low viscosity conditioner that is dispensable through an aerosol and/or pump foamer.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A hair conditioner composition comprising:
  a. a gel network composition comprising:
    from about 1 wt. % to about 10 wt. % of a cationic surfactant comprising a chloride counterion that is behentrimonium chloride; and
    b. from about 1 wt. % to about 10 wt. % of a fatty alcohol:
      wherein the gel network composition comprises all vesicles or mostly vesicles;
    wherein the gel network comprises a shear stress of greater than 50 and less than 200 Pa;
  c. from about 60 wt. % to about 90 wt. % water;
  d. from about 1 wt. % to about 10 wt. % propellant;
    wherein the mole ratio of cationic surfactant to fatty alcohol is from about 0.6 to about 1.1;
    wherein the composition comprises a liquid phase viscosity from about 5 cP to about 10,000 cP;
    wherein the conditioner composition is made by heating the cationic surfactant and the fatty alcohol to at least 70° C., then cooling the cationic surfactant and the fatty alcohol with a cooling bath with a temperature from about 15° C. to about 25° C. lower than the composition to form a gel network base composition, and finally combining the gel network base composition with the water.

2. A method of conditioning hair comprising:
  a. providing a foam dispenser containing a propellant and a conditioner composition comprising:
    i. from about 1% to about 10%, by weight of the conditioning composition, of a cationic surfactant comprising a chloride counterion that is behentrimonium chloride; and from about 1% to about 10%, by weight of the conditioning composition, of a fatty alcohol selected from cetyl alcohol, stearyl alcohol, behenyl alcohol, and mixtures thereof;

ii. a gel network comprising at least a portion of the cationic surfactant and at least a portion of the fatty alcohol;
   wherein the gel network comprises all vesicles or mostly vesicles;
   wherein the gel network comprises a shear stress of greater than 50 and less than 200 Pa;
iii. from about 60 wt. % to about 90 wt. % water;
iv. wherein the mole ratio of cationic surfactant to fatty alcohol is from about 0.6 to about 1.1;
   wherein the composition comprises a liquid phase viscosity from about 5 cP to about 10,000 cP;
wherein the conditioner composition is made by heating the cationic surfactant and the fatty alcohol to at least 70° C., then cooling the cationic surfactant and the fatty alcohol with a cooling bath with a temperature from about 15° C. to about 25° C. lower than the composition to form a gel network base composition, and finally combining the gel network base composition with the water;
b. dispensing the conditioner composition from the foam dispenser as a dosage of foam;
c. applying the foam to the hair;
d. optionally rinsing the foam from the hair.

3. The method of conditioning hair of claim 2, wherein the liquid phase viscosity of the composition is from about 20 cP to about 8000 cP.

4. The method of conditioning hair of claim 2, wherein the liquid phase viscosity of the composition is from about 20 cP to about 5000 cP.

5. The method of conditioning hair of claim 2, wherein an additional cationic surfactant is selected from cetyl trimethyl ammonium chloride, stearyl trimethyl ammonium chloride, ditallow alkyl dimethyl ammonium chloride, dihydrogenated tallow alkyl dimethyl ammonium chloride, distearyl dimethyl ammonium chloride, dicetyl dimethyl ammonium chloride, and combinations thereof.

6. The method of conditioning hair of claim 2, wherein the composition comprises from about 2.5 wt. % to about 6 wt. % cationic surfactant.

7. The method of conditioning hair of claim 2, wherein the composition comprises from about 2.5 wt. % to about 6 wt. % fatty alcohol wherein the fatty alcohol is selected from cetyl alcohol, stearyl alcohol, behenyl alcohol, and combinations thereof.

8. The method of conditioning hair of claim 2, wherein the mole ratio of cationic surfactant to fatty alcohol is from about 0.66 to about 1.

9. The method of conditioning hair of claim 2, wherein the gel network is substantially uniform.

10. The method of claim 2 wherein the foam dispenser is an aerosol dip tube foam dispenser.

11. The method of claim 2 wherein the foam comprises a foam density from about 0.05 g/mL to about 0.35 g/mL.

12. The method of claim 2 wherein the foam comprises a compression force from about 10 g to about 40 g.

13. The method of conditioning hair of claim 2, wherein the gel network is uniform as determined by the Differential Scanning Calorimetry Method.

14. The method of conditioning hair of claim 2, wherein the hair conditioner composition comprising:
a. from about 2% to about 6.5%, by weight of the conditioner composition, of an additional cationic surfactant selected from, cetyl trimethyl ammonium chloride, stearyl trimethyl ammonium chloride, ditallow alkyl dimethyl ammonium chloride, dihydrogenated tallow alkyl dimethyl ammonium chloride, distearyl dimethyl ammonium chloride, dicetyl dimethyl ammonium chloride, and combinations thereof; and
b. from about 2.5% to about 6%, by weight of the conditioner composition, of the fatty alcohol;
wherein the mole ratio of cationic surfactant to fatty alcohol is from about 0.63 to about 1.1.

15. The method of conditioning hair of claim 14, wherein the gel network comprises a shear stress from about 60 Pa to about 195 Pa.

16. The method of conditioning hair of claim 14, wherein the mole ratio of cationic surfactant to fatty alcohol is from about 0.66 to about 1.

* * * * *